United States Patent
Bhattacharya et al.

(10) Patent No.: US 11,059,833 B2
(45) Date of Patent: *Jul. 13, 2021

(54) BCKDK INHIBITORS

(71) Applicant: Pfizer Inc., New York, NY (US)

(72) Inventors: Samit Kumar Bhattacharya, Waltham, MA (US); Leanne Marie Buzon, Stonington, CT (US); Kevin James Filipski, Reading, MA (US); David Andrew Griffith, Sudbury, MA (US); Bethany Lyn Kormos, Somerville, MA (US); Luis Angel Martinez-Alsina, Gales Ferry, CT (US); Russell Alan Miller, Dedham, MA (US); Matthew Richard Reese, Mystic, CT (US); Rachel Jane Roth Flach, Rockland, MA (US); Yuan Zhang, Mansfield, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,257

(22) Filed: Oct. 23, 2020

(65) Prior Publication Data
US 2021/0087204 A1 Mar. 25, 2021

Related U.S. Application Data

(63) Continuation of application No. 16/912,828, filed on Jun. 26, 2020.

(60) Provisional application No. 63/031,719, filed on May 29, 2020, provisional application No. 62/960,817, filed on Jan. 14, 2020, provisional application No. 62/868,057, filed on Jun. 28, 2019.

(51) Int. Cl.
| | |
|---|---|
| C07D 495/04 | (2006.01) |
| A61K 31/155 | (2006.01) |
| A61K 31/4985 | (2006.01) |
| A61K 31/7048 | (2006.01) |
| A61K 45/06 | (2006.01) |

(52) U.S. Cl.
CPC .......... *C07D 495/04* (2013.01); *A61K 31/155* (2013.01); *A61K 31/4985* (2013.01); *A61K 31/7048* (2013.01); *A61K 45/06* (2013.01); *C07B 2200/13* (2013.01)

(58) Field of Classification Search
None
See application file for complete search history.

(56) References Cited

FOREIGN PATENT DOCUMENTS

WO  200190101  11/2001

OTHER PUBLICATIONS

Gronowitz et al., Acta Pharmaceutica Suecica (1978), 15(5), pp. 368-381.*
Chen, M., et al., "Therapeutic Effect of Targeting Branched-Chain Amino Acid Catabolic Flux in Pressure-Overloaded Indcued Heart Failure", Journal of American Heart Association, 2109, pp. 1-20, 8(11).
Ericksen, R., et al., "Loss of BCAA Catabolism during Carcinogenesis Enhances mTORC1 Activity and Promotes Tumor Development and Progression", Cell Metabolism, May 7, 2019, pp. 1151-1165, vol, 29.
International Written Opinion and Search Report dated Aug. 11, 2020 for Application No. PCT/IB2020/056066, filed on Jun. 26, 2020, 15 pages.
Lian, K., et al., "PP2Cm overexpression alleviates MI/R injury medicated by a BCAA catabolism defect and oxidative stress in diabetic mice", European Journal of Pharmacology, 2020, pp. 1-10, 866(172796).
Shin-Chia, Tso, et al., "Benzothiophene Carboxylate Derivatives as Novel Allosteric Inhibitors of Branched-chain [alpha]-Ketoacid Dehydrogenase Kinase", Journal of Biological Chemistry, Jul. 25, 2014, pp. 20583-20593, 289(30).
Tian, Q., et al., "Phosphorylation of BCKDK of BCAA catabolism at Y246 by Scr promotes metastasis of colorectal cancer", Oncogen, Apr. 1, 2020, pp. 3980-3996, vol. 39.
Uddin, G.M., et al., "Impaired branched chain amino acid oxidation contributes to cardiac insulin resistance in heart failure", Cardiovascular Diabetology, 2019, pp. 1-12, 18(86).
Wang, J., et al., "BCAA Catabolic Defect Alters Glucose Metabolism in Lean Mice", Frontiers in Physiology, Sep. 4, 2019, Article 1140, pp. 1-14, vol. 10.
Wright, W.B., "The preparation of 3-chlorothieno[3,2-b] thiophene derivatives from thiaophene-2-acrylic acids", Journal of Heterocyclic Chemistry, Aug. 1, 1972, pp. 879-882, 9(4).

* cited by examiner

*Primary Examiner* — Brian J Davis
(74) *Attorney, Agent, or Firm* — Lisa A. Samuels

(57) ABSTRACT

Described herein are compounds of Formula I,

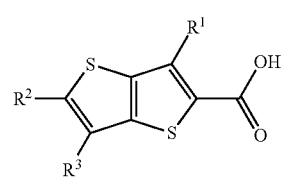

wherein $R^1$, $R^2$, and $R^3$ are defined herein, their use as branched-chain alpha keto acid dehydrogenase kinase inhibitors, pharmaceutical compositions containing such inhibitors and the use of such inhibitors to treat, for example, diabetes, NASH and heart failure.

23 Claims, 2 Drawing Sheets

BCKDK INHIBITORS

CROSS REFERENCE TO PRIOR APPLICATIONS

This application is a CONTINUATION of application Ser. No. 16/912,828, filed Jun. 26, 2020 which claims the benefit of U.S. Provisional Application Ser. No. 63/031,719, filed May 29, 2020 and U.S. Provisional Application Ser. No. 62/960,817, filed Jan. 14, 2020, and U.S. Provisional Application Ser. No. 62/868,057, filed Jun. 28, 2019 under 35 USC 119(e), the disclosures of which are hereby incorporated in their entirety.

FIELD OF THE INVENTION

The present invention provides compounds that are branched-chain alpha keto acid dehydrogenase kinase inhibitors, pharmaceutical compositions containing such inhibitors and the use of such inhibitors to treat for example, diabetes, NASH and heart failure.

BACKGROUND OF THE INVENTION

Branched-chain amino acids (BCAAs) account for about 40% of the essential amino acids in healthy subjects and must be acquired through a well-balanced diet. Branched-chain amino acids are toxic in excess but are required for protein synthesis and cellular signaling processes. BCAAs are transaminated by branched-chain aminotransferase (BCAT) to their alpha-keto acid forms: alpha-ketoisocaproate (KIC/ketoleucine), 2-keto-3-methylvalerate (KMV/ketoisoleucine) and alpha-ketoisovalerate (KIV/ketovaline). The branched-chain keto acids (BCKAs) are then oxidatively decarboxylated by the branched-chain ketoacid dehydrogenase (BCKDH) enzyme complex, which consists of multiple copies of BCKDH E1$\alpha$/$\beta$ tetramers, BCKDH E2, and BCKDH E3 subunits. The complex is regulated by inhibitory phosphorylation, which is mediated by BCKDH kinase (BCKDK), and this same phosphorylation site is dephosphorylated by the phosphatase PPM1K. Inhibition of complex phosphorylation promotes BCKDH activity and thus the irreversible catabolism of BCKA. (Lynch C J, Adams S H: Branched-chain amino acids in metabolic signalling and insulin resistance. Nat Rev Endocrinol 2014, 10:723-36.) Deletion of Bckdk in mice confirms this regulation as mice lacking Bckdk display increased BCKDH activity in multiple tissues. (Joshi M A, Jeoung N H, Obayashi M, Hattab E M, Brocken E G, Liechty E A, Kubek M J, Vattem K M, Wek R C, Harris R A: Impaired growth and neurological abnormalities in branched-chain alpha-keto acid dehydrogenase kinase-deficient mice. Biochem J 2006, 400:153-62.)

U.S. Pat. No. 9,078,865 is directed to for example, methods of decreasing plasma levels of one or more branched-chain amino acids or branched-chain alpha-ketoacids comprising administering to an individual in need thereof a therapeutically effective amount of at least one compound of the formula: phenyl-CH$_2$—(CH$_2$)$_n$—COOH wherein n is 0, 2, 4, 6 or 8 in order to treat for example an inborn error of metabolism in newborns known as maple syrup urine disease (MSUD). MSUD, also called branched-chain ketoaciduria, is an autosomal recessive disorder.

There is a strong correlation with BCAA catabolism and cardiometabolic health. Increased BCAA/BCKA levels have been observed in plasma of type 2 diabetic patients in multiple studies. (Wang T J, Larson M G, Vasan R S, Cheng S, Rhee E P, McCabe E, Lewis G D, Fox C S, Jacques P F, Fernandez C, O'Donnell C J, Carr S A, Mootha V K, Florez J C, Souza A, Melander O, Clish C B, Gerszten R E: Metabolite profiles and the risk of developing diabetes. Nat Med 2011, 17:448-53; Newgard C B, An J, Bain J R, Muehlbauer M J, Stevens R D, Lien L F, Haqq A M, Shah S H, Arlotto M, Slentz C A, Rochon J, Gallup D, Ilkayeva O, Wenner B R, Yancy W S, Jr., Eisenson H, Musante G, Surwit R S, Millington D S, Butler M D, Svetkey L P: A branched-chain amino acid-related metabolic signature that differentiates obese and lean humans and contributes to insulin resistance. Cell Metab 2009, 9:311-26.)

Reduced PPM1K and increased BCKDK levels were observed in human NASH. (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human nonalcoholic fatty liver disease. Amino Acids 2015, 47:603-15.)

Reduced mRNA levels for enzymes in the catabolic pathway have also been observed in skeletal muscle of human diabetic patients. (Lerin C, Goldfine A B, Boes T, Liu M, Kasif S, Dreyfuss J M, De Sousa-Coelho A L, Daher G, Manoli I, Sysol J R, Isganaitis E, Jessen N, Goodyear L J, Beebe K, Gall W, Venditti C P, Patti M E: Defects in muscle branched-chain amino acid oxidation contribute to impaired lipid metabolism. Mol Metab 2016, 5:926-36.)

Similarly, metabolomics and RNA profiling data from mouse hearts also suggest that genes in the BCAA/BCKA catabolic pathway are downregulated in heart failure. (Lai L, Leone T C, Keller M P, Martin O J, Broman A T, Nigro J, Kapoor K, Koves T R, Stevens R, Ilkayeva O R, Vega R B, Attie A D, Muoio D M, Kelly D P: Energy metabolic reprogramming in the hypertrophied and early stage failing heart: a multisystems approach. Circ Heart Fail 2014, 7:1022-31; Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

These data collectively suggest that BCAA catabolism is impaired in multiple human disease states. One mechanism to increase BCAA catabolism is a BCKDK inhibitor. By inhibiting BCKDK, BCKDH activity will increase and BCAA catabolism will be increased. Another mechanism to increase BCAA catabolism is a BCKDK degrader. By degrading BCKDK, BCKDH activity will increase and BCAA catabolism will be increased. Although there has been some early research related to BCKDK there remains a need for pharmaceutical agents that have BCKDK inhibiting and/or degrading activity and are useful in the treatment, prevention or diminution of the manifestations of the maladies described herein.

SUMMARY OF THE INVENTION

The present invention is directed to compounds of Formula I

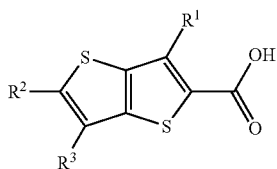

wherein $R^1$ is H, bromo, chloro, fluoro, $(C_1-C_2)$alkyl, or $(C_1-C_2)$ fluoroalkyl;

$R^2$ is fluoro or chloro, wherein if $R^1$ is chloro and $R^3$ is H then $R^2$ is fluoro; and $R^3$ is H, chloro, fluoro, methyl, or $(C_1)$fluoroalkyl, wherein if $R^1$ is H then $R^3$ is chloro, fluoro, methyl or $(C_1)$fluoroalkyl;

or a pharmaceutically acceptable salt of said compound.

The present invention is also directed at methods of treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount of a compound of Formula I or a pharmaceutically acceptable salt of said compound.

The present invention is also directed at methods of treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

The present invention is also directed at methods of treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease including administering to a mammal, such as a human, in need of such treatment a therapeutically effective amount of a compound of Formula I or a pharmaceutically acceptable salt of said compound.

The present invention is also directed at methods of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

The present invention is also directed at pharmaceutical compositions having a therapeutically effective amount of a compound of Formula I or a pharmaceutically acceptable salt of said compound and a pharmaceutically acceptable carrier, vehicle or diluent.

The present invention is also directed at pharmaceutical combination compositions that include: a therapeutically effective amount of a composition having:

a first compound, said first compound being a compound of Formula I or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluent.

It is to be understood that both the foregoing general description and the following detailed description are exemplary and explanatory only and are not restrictive of the invention, as claimed.

DETAILED DESCRIPTION OF THE INVENTION

Figure 1:
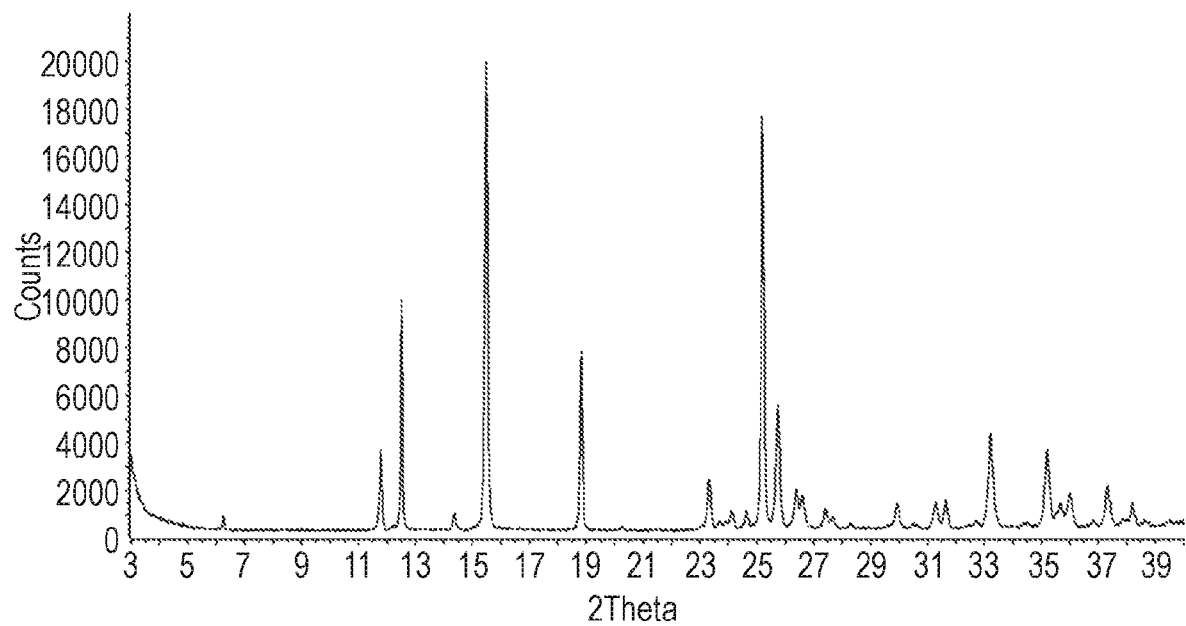
FIG. 1 is a characteristic X-ray powder diffraction pattern showing Example 1, Form 1 (Vertical Axis: Intensity (CPS); Horizontal Axis: Two theta (degrees)).

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting. In this specification and in the claims that follow, reference will be made to a number of terms that shall be defined to have the following meanings:

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated to require a tighter range.

The term "alkyl", alone or in combination, means an acyclic, saturated hydrocarbon group of the formula CnH2n+1 which may be linear or branched. Examples of such groups include methyl, ethyl, n-propyl, isopropyl, butyl, sec-butyl, isobutyl and t-butyl. The carbon atom content of alkyl and various other hydrocarbon-containing moieties is indicated by a prefix designating a lower and upper number of carbon atoms in the moiety, that is, the prefix Ci-Cj indicates a moiety of the integer "i" to the integer "j" carbon atoms, inclusive. Thus, for example, $C_1$-$C_3$ alkyl refers to alkyl of one to three carbon atoms, inclusive.

"Fluoroalkyl" means an alkyl as defined herein substituted with one, two or three fluoro atoms. Exemplary ($C_1$)fluoroalkyl compounds include fluoromethyl, difluoromethyl and trifluoromethyl, exemplary ($C_2$)fluoroalkyl compounds include 1-fluoroethyl, 2-fluoroethyl, 1,1-difluoroethyl, 1,2-difluoroethyl, 1,1,1-trifluoroethyl, 1,1,2-trifluoroethyl, and the like.

"Compounds" when used herein includes any pharmaceutically acceptable derivative or variation, including conformational isomers (e.g., cis and trans isomers) and all optical isomers (e.g., enantiomers and diastereomers), racemic, diastereomeric and other mixtures of such isomers, as well as solvates, hydrates, isomorphs, polymorphs, tautomers, esters, salt forms, and prodrugs. The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the compounds of the present invention include but are not limited to those having a carboxyl moiety wherein the free hydrogen is replaced by ($C_1$-$C_4$)alkyl, ($C_2$-$C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N(alkoxycarbonyl)aminomethyl having from 3 to 9 carbon atoms, 1-(N(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, and ferrets.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits.

"Patient" refers to warm blooded animals such as, for example, guinea pigs, mice, rats, gerbils, cats, rabbits, dogs, cattle, goats, sheep, horses, monkeys, chimpanzees, and humans.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

"Therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "pharmaceutically acceptable" means the substance (e.g., the compounds of the invention) and any salt thereof, or composition containing the substance or salt of the invention that is suitable for administration to a patient.

One embodiment of the present invention includes compounds of Formula I wherein $R^1$ is H, bromo or chloro; $R^2$ is fluoro; and $R^3$ is H or fluoro wherein if $R^1$ is H then $R^3$ is fluoro; or a pharmaceutically acceptable salt of said compound.

Another embodiment of the present invention includes compounds having the structure

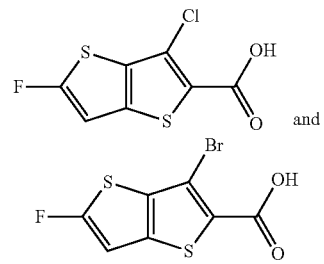

and crystals including said compounds or pharmaceutically acceptable salts thereof.

Another embodiment of the present invention includes use of a compound of Formula I or a pharmaceutically acceptable salt of said compound for use as a medicament in treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula I or a pharmaceutically acceptable salt of said compound for the manufacture of a medicament in treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma including administering to a mammal, such as a human, in need of such treatment a therapeutically effective amount.

Another embodiment of the present invention includes use of a compound of Formula I or a pharmaceutically acceptable salt of said compound for use as a medicament in treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating heart failure, congestive heart failure, coronary heart disease, peripheral vascular disease, renovascular disease, pulmonary hypertension, vasculitis, acute coronary syndromes and modification of cardiovascular risk including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for use as a medicament in treating Type I diabetes, Type diabetes mellitus, idiopathic Type 1 diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia and maple syrup urine disease including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating Type I diabetes, Type diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia and maple syrup urine disease including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for use as a medicament in treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

Another embodiment of the present invention includes use of a compound of Formula I or a pharmaceutically acceptable salt of said compound for the manufacture of a medicament in treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma including administering to a mammal, such as a human, in need of such treatment a therapeutically effective amount of a compound of Formula I or a pharmaceutically acceptable salt of said compound.

The present invention includes all pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, oxygen, such as $^{15}O$, $^{17}O$ and $^{18}O$, and sulphur, such as $^{35}S$.

Certain isotopically-labelled compounds of Formula I for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, and $^{15}O$, can be useful in Positron Emission Tomography (PET) studies for examining substrate receptor occupancy.

Isotopically-labelled compounds of Formula I can generally be prepared by conventional techniques known to those skilled in the art or by processes analogous to those described in the accompanying Examples and Preparations using an appropriate isotopically-labelled reagents in place of the non-labelled reagent previously employed.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization.

Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Salts encompassed within the term "pharmaceutically acceptable salts" refer to the compounds of this invention which are generally prepared by reacting the free acid with a suitable organic or inorganic base to provide a salt of the compound of the invention that is suitable for administration to a patient.

Suitable base salts are formed from bases which form non-toxic salts. Examples include the aluminium, arginine, calcium, choline, diethylamine, glycine, lysine, magnesium, meglumine, olamine, potassium, sodium, trimethamine and zinc salts. Hemisalts of acids and bases may also be formed, for example, hemisulfate and hemicalcium salts. For a review on suitable salts, see *Handbook of Pharmaceutical Salts: Properties, Selection, and Use* by Stahl and Wermuth (Wiley-VCH, 2002).

Hemisalts of bases may also be formed, for example, hemicalcium salts. For a review on suitable salts, see Handbook of Pharmaceutical Salts: Properties, Selection, and Use by Stahl and Wermuth (Wiley-VCH, 2002).

Pharmaceutically acceptable salts of compounds of Formula I may be prepared by one or more of three methods:
(i) by reacting the compound of Formula I with the desired base;
(ii) by removing a base-labile protecting group from a suitable precursor of the compound of the invention or by ring-opening a suitable cyclic precursor, for example, a lactone or lactam, using the desired base; or
(iii) by converting one salt of the compound of the invention to another by reaction with an appropriate base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

The compounds of Formula I, and pharmaceutically acceptable salts thereof, may exist in unsolvated and solvated forms. The term 'solvate' is used herein to describe a molecular complex comprising the compound of Formula I, or a pharmaceutically acceptable salt thereof, and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

Also included within the scope of the invention are active metabolites of compounds of Formula I (including prodrugs), that is, compounds formed in vivo upon administration of the drug, often by oxidation or dealkylation. An example of metabolites in accordance with the invention includes where the compound of Formula I contains a methyl group, a hydroxymethyl derivative thereof ($-CH_3 \rightarrow -CH_2OH$):

The compounds of the invention may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of Formula I may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, $4^{th}$ Edition (Edward Arnold, 1970).

The compounds of Formula I may exhibit polymorphism and/or one or more kinds of isomerism (e.g. optical, geometric or tautomeric isomerism). The compounds of Formula I may also be isotopically labelled. Such variation is implicit to the compounds of Formula I defined as they are by reference to their structural features and therefore within the scope of the invention.

The term "room temperature or ambient temperature" means a temperature between 18 to 25° C., "HPLC" refers to high-pressure liquid chromatography, "MPLC" refers to medium-pressure liquid chromatography, "TLC" refers to thin-layer chromatography, "MS" refers to mass spectrum or mass spectroscopy or mass spectrometry, "NMR" refers to nuclear magnetic resonance spectroscopy, "DCM" refers to dichloromethane, "DMSO" refers to dimethyl sulfoxide, "DME" refers to 1,2-dimethoxyethane, "EtOAc" refers to ethyl acetate, "MeOH" refers to methanol, "Ph" refers to the phenyl group, "Pr" refers to propyl, "trityl" refers to the triphenylmethyl group, "ACN" refers to acetonitrile, "DEAD" refers to diethyl azodicarboxylate, and "DIAD" refers to diisopropyl azodicarboxylate.

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section. Specific synthetic schemes for preparation of the compounds of Formula I are outlined below.

As used herein, the expressions "reaction-inert solvent" and "inert solvent" refer to a solvent or a mixture thereof which does not interact with starting materials, reagents, intermediates or products in a manner which adversely affects the yield of the desired product.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-tert-butoxycarbonyl, benzyloxycarbonyl, and 9-fluorenylmethylenoxycarbonyl for amines and lower alkyl or benzyl esters for carboxylic acids), which are generally not chemically reactive under the reaction conditions described and can typically be removed without chemically altering other functionality in the Formula I compound.

Compounds of Formula I may be prepared according to the Examples provided herein.

The starting materials and reagents for the above described Formula I compounds are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

The present invention is also directed at pharmaceutical compositions having a therapeutically effective amount of a compound of Formula I or a pharmaceutically acceptable salt of said compound and a pharmaceutically acceptable carrier, vehicle or diluent.

The compounds of this invention may also be used in conjunction with other pharmaceutical agents (e.g., antiatherosclerotic and antithrombotic agents) for the treatment of the disease/conditions described herein. The present invention is also directed at pharmaceutical combination compositions that include: a therapeutically effective amount of a composition having:

a first compound, said first compound being a compound of any of Formula I or a pharmaceutically acceptable salt of said compound;

a second compound, said second compound being an anti-diabetic agent; a non-alcoholic steatohepatitis treatment agent, a non-alcoholic fatty liver disease treatment agent or an anti-heart failure treatment agent and a pharmaceutical carrier, vehicle or diluents.

In one embodiment of the present invention, said non-alcoholic steatohepatitis treatment agent or non-alcoholic fatty liver disease treatment agent is an ACC inhibitor, a KHK inhibitor, a DGAT-2 inhibitor, an FXR agonist, metformin, incretin analogs, or an incretin receptor modulator.

In another embodiment of the present invention, said anti-diabetic agent is an SGLT-2 inhibitor, metformin, incretin analogs, an incretin receptor modulator, a DPP-4 inhibitor, or a PPAR agonist.

In another embodiment of the present invention, said anti-diabetic agent is metfomin, sitagliptin or ertuglifozin.

In another embodiment of the present invention, said anti-heart failure agent is an ACE inhibitor, an angiotensin receptor blocker, an angiotensin-receptor neprilysin inhibitor, a beta adrenergic receptor blocker, a calcium channel blocker, or a vasodilator.

While liver biopsy remains the standard for identification of NASH patients, non-invasive methods for identifying patients with inflammatory liver disease have been described by Drescher, H., et al., ("Current status in testing for nonalcoholic fatty liver disease (NAFLD) and non-alcoholic steatohepatitis (NASH), Cells 2019, 8, 845). These non-invasive surrogate markers include, blood tests, liver function tests, and imaging which have been successfully relied upon as a means to identify inflammatory liver disease (hepatic steatosis, steatohepatitis, and fibrosis) and a measure for efficacy of a specific therapy.

Hepatic steatosis (steatosis) is a key factor in NAFLD. While there is no specific serum marker existing today, there are several blood biomarkers panels that can be utilized to assess steatosis. These blood biomarkers may include, but are not limited to: i) NAFLD ridge score (parameters include ALT, HDL, cholesterol, triglycerides, HbA1c, leukocyte count hypertension); ii) NAFLD Liver Fat Score (NLFS) (parameters include liver fat content, metabolic syndrome, type-2 diabetes, AST, AST:ALT, fasting insulin); iii) Hepatic Steatosis Index (HIS) (parameters include AST, ALT, BMI, diabetes, sex); iv) Fatty Liver Index (FLI) (parameters include BMI, waist circumference, triglycerides, γ-glutamyl transferase); v) lipid accumulation product index (LAP) (parameters include sex, triglycerides, weight circumference); vi) Fatty Liver Inhibition of Progression (FLIP) algorithm (parameters include histological steatosis, disease activity, fibrosis score); vii) CHek score (parameters include age, HbA1c, γ-glutamyl transferase, adiponectin, M30); viii) NAFLD Fibrosis Score (NFS) (parameters include AST: ALT, albumin, platelet count, age, BMI, hyperglycemia); ix) Fibrosis-4-Score (FIB-4) (parameters include AST, ALT, platelet count, age); x) AST to Platelet Ratio Index (APRI) (parameters include AST, platelet count); xi) BARD Score (parameters include BMI, AST:ALT, diabetes); xii) Enhanced Liver Fibrosis panel (ELF) (parameters include age, TIMP-1, PIIINP, hyaluronicacid); xiii) Hepascore (parameters include bilirubin, γ-glutamyl transferase, hyaluronic acid, α$_2$ macroglobilin, age, gender); xiv) FibroTest-FibroSURE/Acti-Test (parameters include α$_2$ macroglobulin, haptoglobin, γ-glutamyl transferase, total bilirubin, apolipoprotein A1, ALT, age, gender); and xv) FibroMeter NAFLD index (parameters include platelet count, prothrombin index, ferritin, AST, ALT, body weight, age, liver stiffness determined by vibration controlled transient elastography). The parameters identified for each biomarker assist in the assessment of liver damage/dysfunction (e.g., AST, ALT, γ-GT, platelet count, haptoglobin), lipid metabolism disorders (e.g., cholesterol, triglycerides), diabetes (e.g., HbA1c, fasting insulin level), inflammation (e.g., α$_2$ macroglobulin, ferritin).

Imaging techniques can also be used in conjunction with biopsy and blood biomarkers to identify NAFLD/NASH patients. Imaging techniques include, but are not limited to ultrasound (e.g., contrast-enhanced ultrasound (CEUS)); ultrasound-based elastography (e.g., vibration-controlled transient elastography (VCTE; FibroScan), real-time shear wave elastography (SWE), acoustic radiation force impulse elastography (ARFI), supersonic shear imaging (SSI)); controlled attenuation parameters; magnetic resonance imaging (MRI) such as MRI proton density fat fraction (MRI-PDFF); and magnetic resonance elastography (MRE).

In any of the present embodiments, the administration of the combination in any of the above-mentioned therapeutically effective amounts can be administered once or twice daily.

In any of the present embodiments, the administration of the combination achieves a change in whole liver fat from baseline equal to or greater than about 30%. In other instances, the administration of the combination achieves a change in whole liver fat from baseline equal to or greater than about 50%.

In any of the present embodiments, identification of a patient may be through use of one or more blood marker panels. Suitable blood marker panels include, but are not limited to the group consisting of NAFLD ridge score, NAFLD Liver Fat Score (NLFS), Hepatic Steatosis Index (HIS), Fatty Liver Index (FLI), Lipid accumulation product index (LAP), Fatty Liver Inhibition of Progress (FLIP) algorithm, CHeK score, NALFD Fibrosis Score (NFS), Fibrosis-4 Score (Fib-4), AST to Platelet Ratio Index (APRI), BARD score, Enhanced Liver Fibrosis panel (ELF), Hepascore, FibroTest-FibroSURE/ActiTest, ibroMeter NAFLD index, and any combinations of the foregoing.

In certain embodiments, when a patient is identified as having hepatic steatosis, the blood marker panel utilized is the NAFLD ridge score. In another embodiment, the blood marker panel is NAFLD Liver Fat Score (NLFS). In another embodiment, the blood marker panel is Fatty Liver Index (FLI).

In certain embodiments, when the patient is identified as having steatohepatitis, the blood marker panel utilized is the Fatty Liver Inhibition of Progress (FLIP) algorithm. In another embodiment, the blood marker panel is the CHeK score.

In certain embodiments, when a patient is identified as having fibrosis, the blood marker panel utilized is the NAFLD Fibrosis Score (NFS). In another embodiment, the blood marker panel is the Fibrosis-4 score (Fib-4). In another embodiment, the blood marker panel is the AST to Platelet Ratio Index (APRI). In another embodiment, the blood marker panel is the BARD score.

In certain other embodiments, in the methods described above, the step of identifying a patient with hepatic steatosis, steatohepatitis or both, further includes the use of imaging. The imaging may include, but is not limited to, ultrasound, ultrasound-based elastography, controlled attenuation parameter (CAP), magnetic resonance imaging (MRI), magnetic resonance elastography, or a combination of the foregoing. In one embodiment, the imaging is contrast-enhanced ultrasound (CEUS). In another embodiment, the imaging is ultrasound-based elastography is selected from vibration-controlled transient elastography (VCTE), acoustic radiation force impulse elastography (ARFI), supersonic shear imaging (SSI), or a combination of the foregoing. In another embodiment, the imaging is magnetic resonance imaging (MRI) or alternatively, MRI proton density fat fraction (MRI-PDFF). In another embodiment, the imaging is magnetic resonance elastography.

In addition to the above-mentioned methods and means for identifying inflammatory liver disease in a patient, regulatory authority recognized conditional approval for Phase III studies in NASH is based on histological surrogate markers obtained by liver biopsy. These generally accepted surrogates are i) resolution of NASH without worsening of fibrosis (i.e. a numerical increase in fibrosis stage); ii) a one or more stage reduction in fibrosis without worsening of NASH. Details may be found in: Ratziu, A critical review of endpoints for non-cirrhotic NASH therapeutic trials, Journal of Hepatology, 2018, 68. 353-361, and references therein.

Additionally, regulatory authorities look to a change in the Nonalcoholic Fatty Liver Disease (NAFLD) Activity Score (NAS) from baseline. The NAFLD Activity Score (NAS) is a composite score equal to the sum of the steatosis grade (0-3), lobular inflammation grade (0-3), and hepatocellular ballooning grade (0-2), from centralized pathologist scoring of liver biopsies. The overall scale of the NAS is 0-8, with higher scores indicating more severe disease. The outcome measure, change from baseline in NAFLD Activity Score (NAS), has a possible range from −8 to +8, with negative values indicating a better outcome (improvement) and positive values indicating a worse outcome. Components of the NAS are scored as follows: Steatosis grade 0=<5% steatosis, 1=5-33% steatosis, 2=34-66% steatosis, 3=>66% steatosis. Lobular inflammation grade=amount of lobular inflammation (combines mononuclear, fat granulomas, and polymorphonuclear (pmn) foci): 0=0, 1=<2 under 20× magnification, 2=2-4 under 20× magnification, 3=>4 under 20× magnification. Hepatocellular ballooning 0=none, 1=mild, 2=more than mild.

In addition to the above-mentioned methods, regulatory authority recognized full approval for drugs to treat NASH is based on demonstrating efficacy against one or more clinical measures including (1) progression to cirrhosis on histopathology, (2) reduction in hepatic decompensation events (including hepatic encephalopathy, variceal bleeding, ascites), (3) change in MELD score from less than or equal to 12 to more than 15, (4) liver transplant, or (5) all-cause mortality.

Combination Agents

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases "concurrent administration," "co-administration," "simultaneous administration," and "administered simultaneously" mean that the compounds are administered in combination. Thus, the methods of prevention and treatment described herein include use of combination agents.

The combination agents are administered to a mammal in a therapeutically effective amount. By "therapeutically effective amount" it is meant an amount of a compound of the present invention that, when administered alone or in combination with an additional therapeutic agent to a mammal, is effective to treat the desired disease/condition (e.g., NASH, heart failure or diabetes).

Given the NASH/NAFLD activity of the compounds of this invention, they may be co-administered with other agents for the treatment of non-alcoholic steatohepatitis (NASH) and/or non-alcoholic fatty liver disease (NAFLD) and associated disease/conditions, such as orlistat, TZDs and other insulin-sensitizing agents, FGF21 analogs, metformin, omega-3-acid ethyl esters (e.g. Lovaza), Fibrates, HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)), ezetimibe, probucol, ursodeoxycholic acid, TGR5 agonists, FXR agonists, Vitamin E, betaine, pentoxifylline, CB1 antagonists, carnitine, N-acetylcysteine, Reduced glutathione, lorcaserin, the combination of naltrexone with buprorion, SGLT2 inhibitors (including dapagliflozin, canagliflozin, empagliflozin, tofogliflozin, ertugliflozin, ASP-1941, THR1474, TS-071, ISIS388626 and LX4211 as well as those in WO2010023594), phentermine, topiramate, GLP-1 receptor agonists, GIP receptor agonists, dual GLP-1 receptor/glucagon receptor agonists (i.e., OPK88003, MED10382, JNJ-64565111, NN9277, BI 456906), dual GLP-1 receprtor/GIP receptor agonists (i.e., Tirzepatide (LY3298176), NN9423), Angiotensin-receptor blockers an acetyl-CoA carboxylase (ACC) inhibitor, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a PNPLA3 inhibitor, an FGF21 analog, an FGF19 analog, a PPAR agonist, an FXR agonist, an AMPK activator, an SCD1 inhibitor or an MPO inhibitor.

Exemplary GLP-1 receptor agonists include liraglutide, albiglutide, exenatide, albiglutide, lixisenatide, dulaglutide, semaglutide, HM15211, LY3298176, Medi-0382, NN-9924, TTP-054, TTP-273, efpeglenatide, those described in WO2018109607, and those described in PCT/IB2019/054867 filed Jun. 11, 2019 including the following:

2-({4-[2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-1,3-benzodioxol-4-yl]piperidin-1-yl}methyl)-7-fluoro-1-[(2S)-oxetan-2-ylmethyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-Chloro-2-fluorophenyl)-2-methyl-1,3-benzodioxol-4-yl]piperidin-1-yl}methyl)-3-(1,3-oxazol-2-ylmethyl)-3H-imidazo[4,5-b]pyridine-5-carboxylic acid;
2-({4-[2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-4-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(pyridin-3-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-5-ylmethyl)-1H-benzimidazole-6-carboxylic acid;
2-({4-[2-(4-chloro-2-fluorophenyl)-2-methyl-1,3-benzodioxol-4-yl]piperidin-1-yl}methyl)-1-[(1-ethyl-1H-1,2,3-triazol-5-yl)methyl]-1H-benzimidazole-6-carboxylic acid;
2-({4-[2-(4-chloro-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[2-(4-chloro-2-fluorophenyl)-7-fluoro-2-methyl-1,3-benzodioxol-4-yl]piperidin-1-yl}methyl)-1-[(2S)-oxetan-2-ylmethyl]-1H-benzimidazole-6-carboxylic acid;
2-({4-[2-(4-cyano-2-fluorophenyl)-2-methyl-1,3-benzodioxol-4-yl]piperidin-1-yl}methyl)-1-(1,3-oxazol-2-ylmethyl)-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-7-fluoro-1-[(2S)-oxetan-2-ylmethyl]-1H-benzimidazole-6-carboxylic acid;
2-({4-[(2S)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2S)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;
2-({4-[(2R)-2-(4-Cyano-2-fluorophenyl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;
2-({4-[(2R)-2-(4-chloro-2-fluorophenyl)-2-methyl-1,3-benzodioxol-4-yl]piperidin-1-yl}methyl)-1-[(1-ethyl-1H-imidazol-5-yl)methyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2S)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[(2R)-2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid;

2-({4-[2-(5-Chloropyridin-2-yl)-2-methyl-1,3-benzodioxol-4-yl]piperidin-1-yl}methyl)-1-[(2S)-oxetan-2-ylmethyl]-1H-benzimidazole-6-carboxylic acid, DIAST-X2;
and 2-[(4-{6-[(4-Cyano-2-fluorobenzyl)oxy]pyridin-2-yl}piperidin-1-yl)methyl]-1-[(2S)oxetan-2-ylmethyl]-1H-benzimidazole-6-carboxylic acid, or pharmaceutically acceptable salts thereof.

Exemplary ACC inhibitors include 4-(4-[(1-isopropyl-7-oxo-1,4,6,7-tetrahydro-1'H-spiro[indazole-5,4'-piperidin]-1'-yl)carbonyl]-6-methoxypyridin-2-yl)benzoic acid; and firsocostat (GS-0976) and pharmaceutically acceptable salts thereof.

Exemplary FXR Agonists include tropifexor (2-[(1R,3R,5S)-3-({5-cyclopropyl-3-[2-(trifluoromethoxy)phenyl]-1,2-oxazol-4-yl}methoxy)-8-azabicyclo[3.2.1]octan-8-yl]-4-fluoro-1,3-benzothiazole-6-carboxylic acid); cilofexor (GS-9674); obeticholic acid; LY2562175; Met409; TERN-101; and EDP-305 and pharmaceutically acceptable salts thereof.

Exemplary DGAT2 inhibitors include (S)-2-(5-((3-ethoxypyridin-2-yl)oxy)pyridin-3-yl)-N-(tetrahydrofuran-3-yl)pyrimidine-5-carboxamide;

2-(5-((3-ethoxy-5-fluoropyridin-2-yl)oxy)pyridin-3-yl)-N-((3R,4S)-4-fluoropiperidin-3-yl)pyrimidine-5-carboxamide;

2-(5-((3-ethoxy-5-fluoropyridin-2-yl)oxy)pyridin-3-yl)-N-((3S,5S)-5-fluoropiperidin-3-yl)pyrimidine-5-carboxamide;

2-(5-((3-ethoxypyridin-2-yl)oxy)pyridin-3-yl)-N-((3R,4S)-4-fluoropiperidin-3-yl)pyrimidine-5-carboxamide;

2-(5-((3-ethoxypyridin-2-yl)oxy)pyridin-3-yl)-N-((3R,4R)-4-fluoropiperidin-3-yl)pyrimidine-5-carboxamide;

2-(5-((3-ethoxy-5-fluoropyridin-2-yl)oxy)pyridin-3-yl)-N-((3R,4R)-4-fluoropiperidin-3-yl)pyrimidine-5-carboxamide; and 2-(5-((3-ethoxypyridin-2-yl)oxy)pyridin-3-yl)-N-((3S,5S)-5-fluoropiperidin-3-yl)pyrimidine-5-carboxamide; and pharmaceutically acceptable salts thereof.

Exemplary KHK inhibitors include [(1R,5S,6R)-3-{2-[(2S)-2-methylazetidin-1-yl]-6-(trifluoromethyl)pyrimidin-4-yl}-3-azabicyclo[3.1.0]hex-6-yl]acetic acid and pharmaceutically acceptable salts thereof.

Given the anti-diabetic activity of the compounds of this invention they may be co-administered with other anti-diabetic agents. Suitable anti-diabetic agents include insulin, metformin, GLP-1 receptor agonists (described herein above), an acetyl-CoA carboxylase (ACC) inhibitor (described herein above), SGLT2 inhibitors (described herein above), monoacylglycerol O-acyltransferase inhibitors, phosphodiesterase (PDE)-10 inhibitors, AMPK activators, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, α-amylase inhibitors (e.g., tendamistat, trestatin and AL-3688), an α-glucoside hydrolase inhibitor (e.g., acarbose), α-glucosidase inhibitors (e.g., adiposine, camiglibose, emiglitate, miglitol, voglibose, pradimicin-Q, and salbostatin), PPARγ agonists (e.g., balaglitazone, ciglitazone, darglitazone, englitazone, isaglitazone, pioglitazone and rosiglitazone), PPAR α/γ agonists (e.g., CLX-0940, GW-1536, GW-1929, GW-2433, KRP-297, L-796449, LR-90, MK-0767 and SB-219994), protein tyrosine phosphatase-1B (PTP-1B) inhibitors (e.g., trodusquemine, hyrtiosal extract, and compounds disclosed by Zhang, S., et al., *Drug Discovery Today*, 12(9/10), 373-381 (2007)), SIRT-1 activators (e.g., resveratrol, GSK2245840 or GSK184072), dipeptidyl peptidease IV (DPP-IV) inhibitors (e.g., those in WO2005116014, sitagliptin, vildagliptin, alogliptin, dutogliptin, inagliptin and saxagliptin), insulin secreatagogues, a fatty acid oxidation inhibitors, A2 antagonists, c-jun amino-terminal kinase (JNK) inhibitors, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, insulin mimetics, glycogen phosphorylase inhibitors (e.g. GSK1362885), VPAC2 receptor agonists, glucagon receptor modulators such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611.

Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81 GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Given the anti-heart failure activity of the compounds of the present invention they may be co-administered with other anti-heart failure agents such as ACE inhibitors (e.g. benzepril, zofenopril, captopril, enalapril, fosinopril, lisinopril, perindopril, quinapril, ramipril, trandolapril), Angiotensin II receptor blockers (e.g., candesartan, losartan, valsartan), Angiotensin-receptor blocker/neprilysin inhibitor (sacubitril/valsartan), If channel blocker Ivabradine, Beta-Adrenergic blocking agents (e.g., bisoprolol, metoprolol succinate, carvedilol), Aldosterone antagonists (e.g., spironolactone, eplerenone), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of the present invention may also be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include *digitalis* and ouabain.

In one embodiment, a Formula I compound may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™) hydrochlorothiazide (such as MICROZIDE™ or ORETIC™), benzthiazide, hydroflumethiazide (such as SALURON™), bendroflumethiazide, methylchlorthiazide, polythiazide, trichlormethiazide, and indapamide (such as LOZOL™); (c) phthalimidinetype diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™).

In another embodiment, a compound of Formula I may be co-administered with a loop diuretic. In still another embodiment, the loop diuretic is selected from furosemide and torsemide. In still another embodiment, one or more compounds of Formula I may be co-administered with furosemide. In still another embodiment, one or more compounds of Formula I may be co-administered with torsemide which may optionally be a controlled or modified release form of torsemide.

In another embodiment, a compound of Formula I may be co-administered with a thiazide-type diuretic. In still another embodiment, the thiazide-type diuretic is selected from the group consisting of chlorothiazide and hydrochlorothiazide. In still another embodiment, one or more compounds of Formula I may be co-administered with chlorothiazide. In still another embodiment, one or more compounds of Formula I may be co-administered with hydrochlorothiazide.

In another embodiment, one or more compounds of Formula I may be coadministered with a phthalimidine-type diuretic. In still another embodiment, the phthalimidine-type diuretic is chlorthalidone.

Examples of suitable mineralocorticoid receptor antagonists include sprionolactone and eplerenone.

Examples of suitable phosphodiesterase inhibitors include: PDE III inhibitors (such as cilostazol); and PDE V inhibitors (such as sildenafil).

Those skilled in the art will recognize that the compounds of this invention may also be used in conjunction with other cardiovascular or cerebrovascular treatments including PCI, stenting, drug-eluting stents, stem cell therapy and medical devices such as implanted pacemakers, defibrillators, or cardiac resynchronization therapy.

Particularly when provided as a single dosage unit, the potential exists for a chemical interaction between the combined active ingredients. For this reason, when a Formula I compound and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In combination therapy treatment, both the compounds of this invention and the other drug therapies are administered to mammals (e.g., humans, male or female) by conventional methods.

The Formula I compounds of this invention, their prodrugs and the salts of such compounds and prodrugs are all adapted to therapeutic use as agents that inhibit and or degrade BCKDK in mammals, particularly humans and thus are useful for the treatment of the various conditions (e.g., those described herein) in which such action is implicated.

The disease/conditions that can be treated in accordance with the present invention include, but are not limited to NASH/NAFLD, diabetes, and heart failure and associated disease/conditions.

In particular, inhibition and/or degradation of BCKDK is associated with NASH/NAFLD and associated disease/conditions because Increased BCAA levels were observed in human NASH samples (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human non-alcoholic fatty liver disease. Amino Acids 2015, 47:603-15). Reduced levels of PPM1K mRNA and increased BCKDK protein levels were also observed in human NASH (Lake A D, Novak P, Shipkova P, Aranibar N, Robertson D G, Reily M D, Lehman-McKeeman L D, Vaillancourt R R, Cherrington N J: Branched chain amino acid metabolism profiles in progressive human nonalcoholic fatty liver disease. Amino Acids 2015, 47:603-15).

Treatment of obese mice or rats with a BCKDK inhibitor reduced hepatic steatosis and triglyceride content, and overexpression of PPM1K in rats reduced hepatic triglyceride content (White P J, McGarrah R W, Grimsrud P A, Tso S C, Yang W H, Haldeman J M, Grenier-Larouche T, An J, Lapworth A L, Astapova I, Hannou S A, George T, Arlotto M, Olson L B, Lai M, Zhang G F, Ilkayeva O, Herman M A, Wynn R M, Chuang D T, Newgard CB: The BCKDH Kinase and Phosphatase Integrate BCAA and Lipid Metabolism via Regulation of ATP-Citrate Lyase. Cell Metab 2018, 27(6), 1281-1293).

Further, regulatory authority recognized conditional approval for Phase III studies in NASH is based on histological surrogate markers obtained by liver biopsy. These generally accepted surrogates are i) resolution of NASH without worsening of fibrosis (i.e. a numerical increase in fibrosis stage); ii) a one or more stage reduction in fibrosis without worsening of NASH. Details may be found in: Ratziu, A critical review of endpoints for non-cirrhotic NASH therapeutic trials, Journal of Hepatology, 2018, 68. 353-361, and references therein.

Accordingly, given the positive correlation between activation of BCKDK with the development of NASH/NAFLD and associated disease/conditions, Formula I compounds of this invention, their prodrugs and the salts of such compounds and prodrugs, by virtue of their pharmacologic action, are useful for the prevention, arrestment and/or regression of fatty liver, nonalcoholic fatty liver disease, nonalcoholic steatohepatitis, nonalcoholic steatohepatitis with liver fibrosis, nonalcoholic steatohepotitis with cirrhosis, nonalcoholic steatohepatitis with cirrhosis and hepatocellular carcinoma and nonalcoholic steatohepatitis with cirrhosis and with a metabolic-related disease.

Similarly, Formula I compounds of this invention, their prodrugs and the salts of such compounds and prodrugs, by virtue of their pharmacologic action, are useful for the prevention, arrestment and/or regression of alcoholic fatty liver disease, alcoholic steatohepatitis, alcoholic steatohepatitis with liver fibrosis, alcoholic steatohepatitis with cirrhosis, alcoholic steatohepatitis with cirrhosis and with hepatocellular carcinoma, and alcoholic steatohepatitis with cirrhosis and with a metabolic-related disease.

In addition, increased BCKDK is associated with heart failure and associated disease/conditions because an increase in BCKA have been observed in hearts from patients with heart failure. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

In heart failure, the regulatory phosphatase that activates BCKDH (PPM1K) is downregulated, and BCKDK is upregulated; thus BCAA catabolism is likely impaired in heart failure. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

Both BCKDH and BCKDK are expressed ubiquitously; however, the regulatory phosphatase PPM1K, which dephosphorylates BCKDH, is expressed most highly in cardiac tissue. Mice lacking PPM1K develop aging-induced heart failure and have worsened heart function when subjected to a transverse aortic constriction (TAC) heart failure model. (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49.)

Use of an inhibitor of BCKDK improved cardiac function in three different preclinical heart failure models (TAC, left anterior descending artery ligation/myocardial infarct, and ischemia/reperfusion). (Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y: Catabolic Defect of Branched-Chain Amino Acids Promotes Heart Failure. Circulation 2016, 133:2038-49; Wang W, Zhang F, Xia Y, Zhao S, Yan W, Wang H, Lee Y, Li C, Zhang L, Lian K, Gao E, Cheng H, Tao L: Defective branched chain amino acid catabolism contributes to cardiac dysfunction and remodeling following myocardial infarction. Am J Physiol Heart Circ Physiol 2016, 311:H1160-H9; Li T, Zhang Z, Kolwicz S C, Jr., Abell L, Roe N D, Kim M, Zhou B, Cao Y, Ritterhoff J, Gu H, Raftery D, Sun H, Tian R: Defective Branched-Chain Amino Acid Catabolism Disrupts Glucose Metabolism and Sensitizes the Heart to Ischemia-Reperfusion Injury. Cell Metab 2017, 25:374-85.)

Therefore, inhibiting/degrading BCKDK in cardiac or peripheral tissue should demonstrate benefit for metabolic disease and cardiac function.

Accordingly, given the positive correlation between activation of BCKDK with the development of heart failure and associated disease/conditions, Formula I compounds of this invention, their prodrugs and the salts of such compounds and prodrugs, by virtue of their pharmacologic action, are useful for the prevention, arrestment and/or regression of heart failure, congestive heart failure, unstable angina, peripheral arterial disease, pulmonary hypertension, vasculitis or where the mammal has experienced myocardial infarction (secondary prevention ($2^{nd}$ myocardial infarction)).

In addition, increased BCKDK is associated with diabetes and associated disease/conditions because plasma BCAA are upregulated in patients with increased fasting glucose levels, and a one standard deviation increase in BCKA concentrations in plasma increases the likelihood of developing diabetes by over 50%. (Wang T J, Larson M G, Vasan R S, Cheng S, Rhee E P, McCabe E, Lewis G D, Fox C S, Jacques P F, Fernandez C, O'Donnell C J, Carr S A, Mootha V K, Florez J C, Souza A, Melander O, Clish C B, Gerszten R E: Metabolite profiles and the risk of developing diabetes. Nat Med 2011, 17:448-53; Newgard C B, An J, Bain J R, Muehlbauer M J, Stevens R D, Lien L F, Haqq A M, Shah S H, Arlotto M, Slentz C A, Rochon J, Gallup D, Ilkayeva O, Wenner B R, Yancy W S, Jr., Eisenson H, Musante G, Surwit R S, Millington D S, Butler M D, Svetkey L P: A branched-chain amino acid-related metabolic signature that differentiates obese and lean humans and contributes to insulin resistance. Cell Metab 2009, 9:311-26; Menni C, Fauman E, Erte 1, Perry J R, Kastenmuller G, Shin S Y, Petersen A K, Hyde C, Psatha M, Ward K J, Yuan W, Milburn M, Palmer C N, Frayling™, Trimmer J, Bell J T, Gieger C, Mohney R P, Brosnan M J, Suhre K, Soranzo N, Spector T D: Biomarkers for type 2 diabetes and impaired fasting glucose using a nontargeted metabolomics approach. Diabetes 2013, 62:4270-6.)

Genetic analyses suggest that loss of function mutations in the PPM1K locus increase BCAA/BCKA levels and are associated with development of type 2 diabetes. (Lotta L A, Scott R A, Sharp S J, Burgess S, Luan J, Tillin T, Schmidt A F, Imamura F, Stewart I D, Perry J R, Marney L, Koulman A, Karoly E D, Forouhi N G, Sjogren R J, Naslund E, Zierath J R, Krook A, Savage D B, Griffin J L, Chaturvedi N, Hingorani A D, Khaw K T, Barroso I, McCarthy M I, O'Rahilly S, Wareham N J, Langenberg C: Genetic Predisposition to an Impaired Metabolism of the Branched-Chain Amino Acids and Risk of Type 2 Diabetes: A Mendelian Randomisation Analysis. PLoS Med 2016, 13:e1002179.)

Treatment of diabetic, obese mice or rats with a BCKDK inhibitor improved fasting glycemia, glycemia in a glucose tolerance test, reduced insulin levels, and improved insulin sensitivity. Overexpression of PPM1K in rats also improved glycemia and reduced insulin levels. (White P J, McGarrah R W, Grimsrud P A, Tso S C, Yang W H, Haldeman J M, Grenier-Larouche T, An J, Lapworth A L, Astapova I, Hannou S A, George T, Arlotto M, Olson L B, Lai M, Zhang G F, Ilkayeva O, Herman M A, Wynn R M, Chuang D T, Newgard C B: The BCKDH Kinase and Phosphatase Integrate BCAA and Lipid Metabolism via Regulation of ATP-Citrate Lyase. Cell Metab 2018, 27 (60, 1281-1293.)

Accordingly, given the positive correlation between BCKDK and the development of diabetes and associated disease/conditions, Formula I compounds of this invention, their prodrugs and the salts of such compounds and prodrugs, by virtue of their pharmacologic action, are useful for the prevention, arrestment and/or regression of Type I diabetes, Type diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertrygliceridemia, insulin resistance, impaired glucose metabolism, skin and connective tissue disorders, foot ulcerations and ulcerative colitis, endothelial dysfunction and impaired vascular compliance, and hyper apo B lipoproteinemia.

The utility of the Formula I compounds of the invention, their prodrugs and the salts of such compounds and prodrugs as medical agents in the treatment of the above described disease/conditions in mammals (e.g. humans, male or female) is demonstrated by the activity of the compounds of this invention in conventional in vitro and in vivo assays described below. The in vivo assays (with appropriate modifications within the skill in the art) may be used to determine the activity of other agents as well as the compounds of this invention. Such assays also provide a means whereby the activities of the Formula I compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

Administration of the compounds of this invention can be via any method which delivers a compound of this invention systemically and/or locally. These methods include oral routes, parenteral, intraduodenal routes, buccal, intranasal etc. Generally, the compounds of this invention are administered orally, but parenteral administration (e.g., intravenous, intramuscular, subcutaneous or intramedullary) may be utilized, for example, where oral administration is inappropriate for the target or where the patient is unable to ingest the drug.

For administration to human patients, an oral daily dose of the compounds herein may be in the range 1 mg to 5000 mg depending, of course, on the mode of and frequency of administration, the disease state, and the age and condition of the patient, etc. An oral daily dose is in the range of 3 mg to 2000 mg may be used. A further oral daily dose is in the range of 5 mg to 1000 mg. For convenience, the compounds of the present invention can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the compound of the present invention. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjuction with the Formula I compounds is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated, each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The present invention further comprises use of a compound of Formula I for use as a medicament (such as a unit dosage tablet or unit dosage capsule). In another embodiment, the present invention comprises the use of a compound of Formula I for the manufacture of a medicament (such as a unit dosage tablet or unit dosage capsule) to treat one or more of the conditions previously identified in the above sections discussing methods of treatment.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds of the invention or combinations can be administered alone but will generally be administered in an admixture with one or more suitable pharmaceutical excipients, adjuvants, diluents or carriers known in the art and selected with regard to the intended route of administration and standard pharmaceutical practice. The compound of the invention or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the invention or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol® brand caprylic/capric acid ester with glycerine or propylene glycol (e.g., Miglyol® 812, Miglyol® 829, Miglyol® 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multiparticulate preparations (granules). In such solid dosage forms, a compound of the present invention or a combination is admixed with at least one inert excipient, diluent or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-Sol™), polyacrilin potassium (an ion exchange resin) and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate and the like); (h) one or more adsorbents (e.g., kaolin, bentonite and the like); and/or (i) one or more lubricants (e.g., talc, calcium stearate, magnesium stearate, stearic acid, polyoxyl stearate, cetanol, talc, hydrogenated caster oil, sucrose esters of fatty acid, dimethylpolysiloxane, microcrystalline wax, yellow beeswax, white beeswax, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% of the formulation and preferably less than 95%, for example 93.5%. Preferred disintegrants include Ac-di-Sol™, Explotab™, starch and sodium lauryl sulphate. When present a disintegrant will usually comprise less than 10% of the formulation or less than 5%, for example about 3%. A preferred lubricant is magnesium stearate.

When present a lubricant will usually comprise less than 5% of the formulation or less than 3%, for example about 1%.

Tablets may be manufactured by standard tabletting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyole® (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the invention or combinations include solutions, wherein the active compound is fully dissolved. Examples of solvents include all pharmaceutically precedented solvents suitable for oral administration, particularly those in which the compounds of the invention show good solubility, e.g., polyethylene glycol, polypropylene glycol, edible oils and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglyides, from Gattefosse), Captex™ 500P (glyceryl triacetate i.e. triacetin, from Abitec), Capmul™ MCM (medium chain mono- and diglycerides, fromAbitec), Migyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture and viscosity modifiers and solubilizers.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of the present invention or combinations include ointments, creams, lotions, powders and sprays. The drugs are admixed with a pharmaceutically acceptable excipient, diluent or carrier, and any preservatives, buffers, or propellants that may be required.

Many of the present compounds are poorly soluble in water, e.g., less than about 1 µg/mL. Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the invention. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material which has essentially no order, but also material which may have some small degree of order, but the order is in less than three dimensions and/or is only over short distances. Amorphous material may be characterized by techniques known in the art such as powder X-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

Water-soluble polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60%) of the poorly soluble compound being in the amorphous state. Such processes include mechanical, thermal and solvent processes. Exemplary mechanical processes include milling and extrusion; melt processes including high temperature fusion, solvent-modified fusion and melt-congeal processes; and solvent processes including non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium and high grades as Aqoa.sup.(R)-LF, Aqoat.sup.(R)-MF and Aqoat.sup.(R)-HF respectively from Shin-Etsu Chemical Co., LTD, Tokyo, Japan. The higher MF and HF grades are generally preferred.

The following paragraphs describe exemplary formulations, dosages, etc. useful for non-human animals. The administration of the compounds of the present invention and combinations of the compounds of the present invention with anti-obesity agents can be effected orally or non-orally.

An amount of a compound of the present invention or combination of a compound of the present invention with another anti-obesity agent is administered such that an effective dose is received. Generally, a daily dose that is administered orally to an animal is between about 0.01 and about 1,000 mg/kg of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself, that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about 0.001 to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

Paste Formulations may be prepared by dispersing the drug in a pharmaceutically acceptable oil such as peanut oil, sesame oil, corn oil or the like.

Pellets containing an effective amount of a compound of the present invention, pharmaceutical composition, or combination may be prepared by admixing a compound of the present invention or combination with a diluent such as carbowax, carnuba wax, and the like, and a lubricant, such as magnesium or calcium stearate, may be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the compound of the invention, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The compounds herein may be formulated for oral, buccal, intranasal, parenteral (e.g., intravenous, intramuscular or subcutaneous) or rectal administration or in a form suitable for administration by inhalation. The compounds of the invention may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences*, 20th Edition (Lippincott Williams & Wilkins, 2000).

Pharmaceutical compositions according to the invention may contain 0.1%-95% of the compound(s) of this invention, preferably 1%-70%. In any event, the composition to be administered will contain a quantity of a compound(s) according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises a means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Also, as the present invention has an aspect that relates to the treatment of the disease/conditions described herein with a combination of active ingredients which may be administered jointly, the invention also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics, Aldrich® Sure/Seal™ from Sigma-Aldrich, or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Products were generally dried under vacuum before being carried on to further reactions or submitted for biological testing. Mass spectrometry data is reported from liquid chromatography-mass spectrometry (LCMS), atmospheric pressure chemical ionization (APCI) instrumentation. Chemical shifts for nuclear magnetic resonance (NMR) data are expressed in parts per million (ppm, δ) referenced to residual peaks from the deuterated solvents employed Reactions proceeding through detectable intermediates were generally monitored by LCMS, and allowed to proceed to full conversion prior to addition of subsequent reagents. For syntheses referencing procedures in other Examples or Methods, reaction conditions (reaction time and temperature) may vary. In general, reactions were monitored by thin-layer chromatography or mass spectrometry, and subjected to work-up when appropriate. Purifications may vary between experiments: in general, solvents and the solvent ratios used for eluents/gradients were chosen to provide appropriate Rfs or retention times. All starting materials in these Preparations and Examples are either commercially available or can be prepared by methods known in the art or as described herein.

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England) and Tyger Scientific (Princeton, N.J.). Certain common abbreviations and acronyms have been employed which may include: AcOH (acetic acid), DBU (1,8-diazabicyclo[5.4.0]undec-7-ene), CDI (1,1'-carbonyldiimidazole), DCM (dichloromethane), DEA (diethylamine), DIPEA (N,N-diisopropylethylamine), DMAP (4-dimethylaminopyridine), DMF (N,N-dimethylformamide), DMSO (dimethyl sulfoxide), EDCI [N-(3-dimethylaminopropyl)-N'-ethylcarbodiimide], $Et_2O$ (diethyl ether), EtOAc (ethyl acetate), EtOH (ethanol), HATU [2-(1H-7-azabenzotriazol-1-yl)-1,1,3,3-tetramethyl uronium hexafluorophosphate methanaminium], HBTU (O-benzotriazol-1-yl-N,N,N',N'-tetramethyluronium hexafluoro phosphate), HOBT (1-hydroxybenzotriazole), IPA (2-propanol), KHMDS [potassium bis(trimethylsilyl)amide], MeOH (methanol), MTBE (tert-butyl methyl ether), $NaBH(OAc)_3$ (sodium triacetoxyborohydride), NaHMDS [sodium bis(trimethylsilyl)amide], NMP (N-methylpyrrolidone), SEM {[2-(trimethylsilyl)ethoxy]methyl}, TEA (triethylamine), TFA (trifluoroacetic acid), THF (tetrahydrofuran), and $T_3P$ (propane phosphonic acid anhydride).

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wis. or DriSolv™ products from EMD Chemicals, Gibbstown, N.J.) were employed. Commercial solvents and reagents were used without further purification. When indicated, reactions were heated by microwave irradiation using Biotage Initiator or Personal Chemistry Emrys Optimizer microwaves or the like. Reaction progress was monitored using thin-layer chromatography (TLC), liquid chromatography-mass spectrometry (LCMS) and high-performance liquid chromatography (HPLC) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, and/or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers or similar equipment. The column eluent was analyzed using a Waters ZQ mass spectrometer scanning in both positive and negative ion modes from 100 to 1200 Da. Other similar instruments were also used. HPLC data were acquired on an Agilent 1100 Series instrument using Gemini or XBridge C18 columns, acetonitrile/water gradients, and either trifluoroacetic acid or ammonium hydroxide modifiers and comparable equipment. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges and the like. Chiral purifications were performed by chiral supercritical fluid chromatography (SFC) using Berger or Thar instruments and similar instruments; ChiralPAK-AD, -AS, -IC, Chiralcel-OD, or -OJ columns; and $CO_2$ mixtures with MeOH, EtOH, iPrOH, or acetonitrile, alone or modified using trifluoroacetic acid or $iPrNH_2$. UV detection was used to trigger fraction collection.

Mass spectrometry data are reported from LCMS analyses. Mass spectrometry (MS) was performed via atmospheric pressure chemical ionization (APCI), electrospray Ionization (ESI), electron impact ionization (EI) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian spectrometers. Chemical shifts are expressed in parts per million (ppm, δ) referenced to the deuterated solvent residual peaks. The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using a medium pressure Biotage or ISCO systems using columns pre-packaged by various commercial vendors including Biotage and ISCO. Unless otherwise noted, chemical reactions were performed at room temperature (about 23 degrees Celsius).

The compounds and intermediates described below were named using the naming convention provided with ACD/ChemSketch 2017.2.1, File Version N40E41, Build 96719 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

The terms "concentrated", "evaporated", and "concentrated in vacuo" refer to the removal of solvent at reduced pressure on a rotary evaporator with a bath temperature less than 60° C. The abbreviation "min" and "h" stand for "minutes" and "hours" respectively. "Room temperature" or "ambient temperature" means a temperature between 15° C. and 25° C., and "UPLC" refers to ultra-performance liquid chromatography, Hydrogenation may be performed in a Parr shaker under pressurized hydrogen gas, or in a Thales-nano H-Cube flow hydrogenation apparatus at full hydrogen and a flow rate between 1-2 mL/min at specified temperature.

HPLC, UPLC, LCMS, and SFC retention times were measured using the methods noted in the procedures.

Example 1

3-Chloro-5-fluorothieno[3,2-b]thiophene-2-carboxylic acid (1)

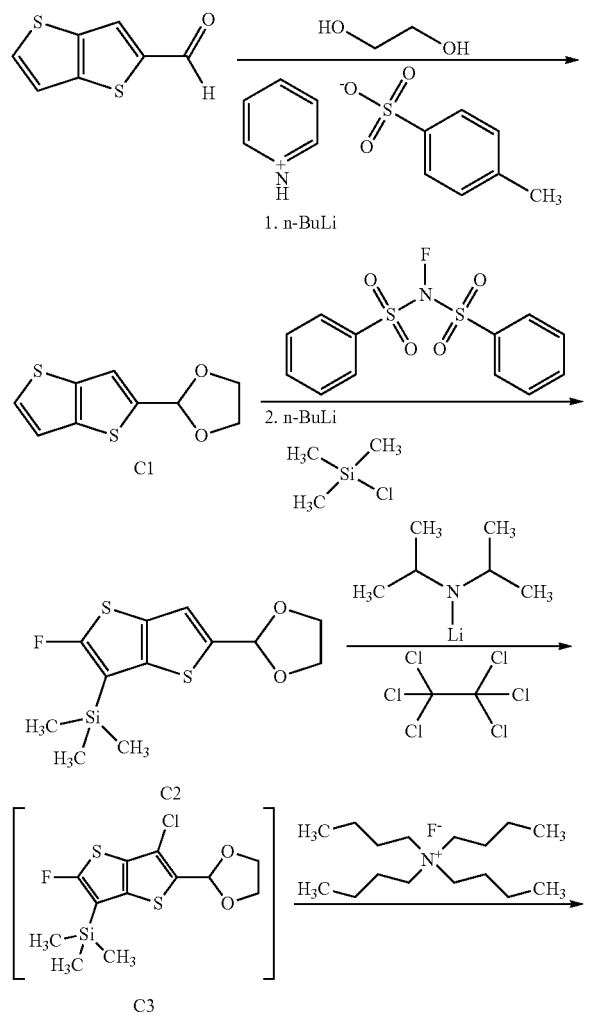

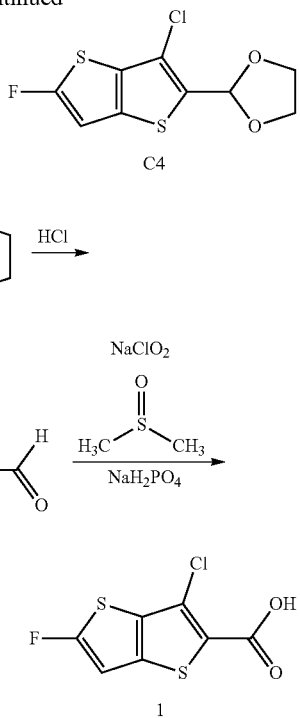

Step 1. Synthesis of 2-(thieno[3,2-b]thiophen-2-yl)-1,3-dioxolane (C1)

This reaction was carried out in three parallel batches. Pyridinium p-toluenesulfonate (11.2 g, 44.6 mmol) was added to a solution of ethylene glycol (133 mL, 2.38 mol) and thieno[3,2-b]thiophene-2-carbaldehyde (100 g, 594 mmol) in toluene (1 L), and the reaction mixture was heated at 125° C. for 16 hours, in an apparatus equipped with a Dean-Stark trap. The resulting mixture was washed sequentially with water (3×1 L) and saturated aqueous sodium carbonate solution (1 L), and the organic layer was dried over sodium sulfate, filtered, and concentrated in vacuo. Silica gel chromatography (Gradient: 1% to 25% ethyl acetate in petroleum ether) afforded $C_1$ as a white solid. Combined yield: 264 g, 1.24 mol, 70%. GCMS m/z 212 [M+]. $^1$H NMR (400 MHz, chloroform-d) δ 7.38 (d, J=5.3 Hz, 1H), 7.35 (br s, 1H), 7.24 (dd, J=5.3, 0.7 Hz, 1H), 6.17 (s, 1H), 4.20-4.00 (m, 4H).

Step 2. Synthesis of [5-(1,3-dioxolan-2-yl)-2-fluorothieno[3,2-b]thiophen-3-yl](trimethyl)silane (C2)

A solution of C1 (40.0 g, 188 mmol) in a mixture of toluene (920 mL) and tetrahydrofuran (720 mL) was cooled to −78° C. n-Butyllithium (2.5 M solution in hexanes; 82.9 mL, 207 mmol) was added in a drop-wise manner, at a rate such that the internal temperature of the reaction mixture remained below −72° C. After the addition had been completed, the reaction mixture was stirred at −78° C. for 2 hours, whereupon a solution of N-fluoro-N-(phenylsulfonyl)benzenesulfonamide (71.3 g, 226 mmol) in tetrahydrofuran (200 mL) was added in a drop-wise manner using an addition funnel, at a rate that maintained the internal reaction temperature below −72° C. The reaction mixture was allowed to stir at −78° C. for 1 hour, and then quenched at −78° C. by addition of saturated aqueous sodium bicarbonate solution (1.5 L). After the resulting mixture had warmed to room temperature, the organic layer was washed with aqueous sodium bicarbonate solution (3×500 mL), and the combined aqueous layers were extracted with ethyl acetate (500 mL). The ethyl acetate extract was washed with aqueous sodium bicarbonate solution (3×200 mL) and then combined with the first organic layer, dried over sodium sulfate, filtered, and concentrated in vacuo. The resulting solid was triturated with a mixture of heptane and diethyl ether (1:1; 250 mL), and the supernatant was decanted, leaving a sticky solid. This solid was again triturated with a mixture of heptane and diethyl ether (1:1; 2×100 mL), and the supernatant was decanted; the combined decanted solutions were concentrated under reduced pressure to provide a greenish solid (39 g).

This solid (39 g) was dissolved in a mixture of toluene (760 mL) and tetrahydrofuran (608 mL), cooled to −78° C., and treated in a drop-wise manner with n-butyllithium (2.5 M solution in hexanes; 98.0 mL, 245 mmol) at a rate that maintained the internal reaction temperature below −72° C. After the reaction mixture had been stirred at −78° C. for 1 hour, a solution of trimethylsilyl chloride (31.1 mL, 245 mmol) in tetrahydrofuran (35 mL) was added, while again maintaining the internal reaction temperature below −72° C. The reaction mixture was then stirred at −78° C. for 45 minutes, whereupon an aliquot was partitioned between diethyl ether and saturated aqueous sodium bicarbonate solution. GCMS analysis of the organic layer of this aliquot indicated conversion to C2: GCMS m/z 302.1 [M$^+$]. The reaction mixture was quenched at −78° C. by addition of saturated aqueous sodium bicarbonate solution (1.5 L), and the resulting mixture was allowed to warm to room temperature. The organic layer was washed with aqueous sodium bicarbonate solution (3×500 mL), and the combined aqueous layers were extracted with ethyl acetate (500 mL). The ethyl acetate extract was washed with aqueous sodium bicarbonate solution (3×200 mL) and then combined with the first organic layer, dried over sodium sulfate, filtered, and concentrated in vacuo. The residue was dissolved in dichloromethane (30 mL) and treated with silica gel (180 g); the resulting slurry was loaded on top of a plug of diatomaceous earth and eluted with dichloromethane (4 L) until C2 ceased to elute. Concentration of these fractions under reduced pressure provided an oily, orange residue (49 g), which was purified via silica gel chromatography (Eluent: 30% dichloromethane in heptane) to afford C2 as a yellow solid. Yield: 36.0 g, 119 mmol, 63%. $^1$H NMR (400 MHz, methanol-d4) δ 7.34 (s, 1H), 6.10 (s, 1H), 4.15-3.96 (m, 4H), 0.39 (s, 9H).

Step 3. Synthesis of 2-(3-chloro-5-fluorothieno[3,2-b]thiophen-2-yl)-1,3-dioxolane (C4)

Lithium diisopropylamide (2.0 M solution in tetrahydrofuran/heptane/ethylbenzene; 90.3 mL, 181 mmol) was added in a drop-wise manner to a −78° C. solution of C2 (36.4 g, 120 mmol) in tetrahydrofuran (1.2 L), at a rate that maintained the internal temperature below −72° C. After completion of the addition, the reaction mixture was allowed to stir at −78° C. for 3 hours, whereupon a solution of hexachloroethane (37.0 g, 156 mmol) in tetrahydrofuran (60 mL) was added drop-wise, in a manner that maintained the internal reaction temperature below −72° C. The reaction mixture was stirred for a further 30 minutes at −78° C., at which time the cooling bath was removed, and the reaction mixture was allowed to warm to room temperature overnight. An aliquot of the reaction mixture was partitioned between diethyl ether and saturated aqueous sodium bicarbonate solution; GCMS analysis of the organic layer indicated conversion to intermediate C3 {[6-chloro-5-(1,3-dioxolan-2-yl)-2-fluorothieno[3,2-b]thiophen-3-yl](trimethyl)silane}: GCMS m/z 336.1 [M$^+$]. The reaction mixture was diluted with saturated aqueous sodium bicarbonate solution and extracted three times with ethyl acetate. The combined organic extracts were washed with saturated aqueous sodium chloride solution, dried over sodium sulfate, filtered, and concentrated in vacuo to provide C3 as a dark amber oil (40.5 g). This material was dissolved in tetrahydrofuran (1.13 L) and treated with water (7.36 mL, 408 mmol), followed by tetrabutylammonium fluoride (1 M solution in tetrahydrofuran; 180 mL, 180 mmol). After the reaction mixture had been stirred at room temperature for 15 minutes, GCMS analysis indicated conversion to C4: GCMS m/z 264.0 [M$^+$]. The reaction mixture was poured into saturated aqueous sodium bicarbonate solution, and extracted three times with ethyl acetate; the combined organic layers were washed with saturated aqueous sodium chloride solution, dried over sodium sulfate, filtered, and concentrated under reduced pressure. Silica gel chromatography (Gradient: 0% to 5% ethyl acetate in heptane) provided C4 as an oily, orange residue. Yield: 17.2 g, 65.0 mmol, 54%. $^1$H NMR (400 MHz, methanol-d$_4$) δ 7.02 (d, J=1.6 Hz, 1H), 6.19 (s, 1H), 4.17-3.97 (m, 4H).

Step 4. Synthesis of 3-chloro-5-fluorothieno[3,2-b]thiophene-2-carbaldehyde (C5)

A solution of hydrogen chloride in 1,4-dioxane (4.0 M; 163 mL, 652 mmol) was added to a solution of C4 (17.2 g, 65.0 mmol) in a mixture of 1,4-dioxane (575 mL) and water (57.5 mL). The reaction mixture was stirred at room temperature for 1 hour, whereupon it was partitioned between ethyl acetate (200 mL) and water (500 mL). The organic layer was washed with saturated aqueous sodium chloride solution (500 mL). The saturated aqueous sodium chloride layer was combined with the original aqueous layer and extracted with ethyl acetate (2×200 mL); these extracts were combined with the first organic layer, dried over sodium sulfate, filtered, and concentrated in vacuo to provide a brown solid. This solid was mixed with pentane (100 mL) and stirred vigorously for 20 minutes at room temperature. The resulting solid was collected via filtration and washed with pentane (3×20 mL), affording C5 as an off-white solid. Yield: 13.0 g, 58.9 mmol, 91%. GCMS m/z 191.0 [M−CHO]$^+$. $^1$H NMR (400 MHz, chloroform-d) δ 10.07 (s, 1H), 6.87 (d, J=1.2 Hz, 1H).

Step 5. Synthesis of 3-chloro-5-fluorothieno[3,2-b]thiophene-2-carboxylic acid (1)

A solution of sodium chlorite (20.5 g, 227 mmol) and sodium dihydrogen phosphate (27.5 g, 229 mmol) in water (100 mL) was added slowly, in a drop-wise manner, to a 0° C. solution of C5 (10.0 g, 45.3 mmol) in a mixture of dimethyl sulfoxide (56 mL) and 2-methyltetrahydrofuran (100 mL). The reaction mixture was then allowed to warm to room temperature, and was stirred at that temperature until the starting material had been completely consumed, as assessed by LCMS analysis (approximately 2 hours). The reaction mixture was then poured in portions into a cold (0° C.) saturated aqueous solution of sodium thiosulfate pentahydrate (300 mL), at a rate that maintained the temperature of the resulting mixture below 15° C. After stirring at 10° C. for 20 minutes, the mixture was diluted with ethyl acetate (200 mL). The aqueous layer was extracted with ethyl acetate (2×200 mL), and the combined organic layers were washed with saturated aqueous sodium chloride solution, dried over magnesium sulfate, filtered, and concentrated in vacuo. The residue was stirred in a mixture of heptane and ethyl acetate (9:1, 50 mL) for about 1 hour. The resulting solid was collected via filtration and washed with a mixture of heptane and ethyl acetate (9:1, 2×20 mL), providing a white solid (10.58 g). This was stirred in dichloromethane for 20 minutes and filtered, the filter cake was washed with dichloromethane (2×20 mL) to afford 3-chloro-5-fluorothieno[3,2-b]thiophene-2-carboxylic acid as a white solid. Yield: 10.0 g, 42.2 mmol, 93%. LCMS m/z 191.0 (chlorine isotope pattern observed) [(M–CO$_2$)—H]$^-$. $^1$H NMR (400 MHz, DMSO-d$_6$) δ 13.5 (br s, 1H), 7.41 (d, J=1.7 Hz, 1H).

Example 2

3-Bromo-5-fluorothieno[3,2-b]thiophene-2-carboxylic acid (2)

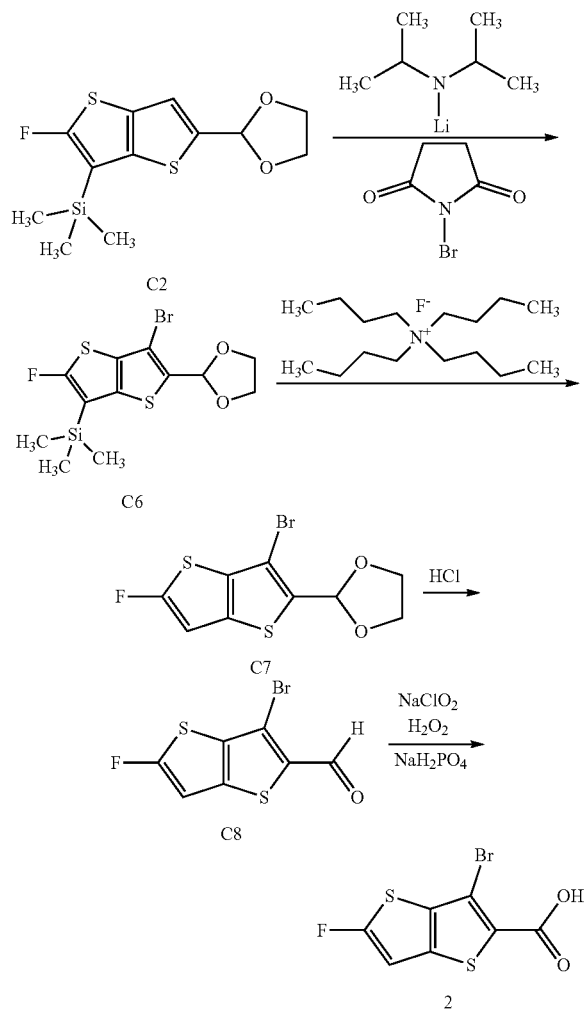

Step 1. Synthesis of [6-bromo-5-(1,3-dioxolan-2-yl)-2-fluorothieno[3,2-b]thiophen-3-yl](trimethyl)silane (C6)

Lithium diisopropylamide solution (2 M; 9.31 mL, 18.6 mmol) was added in a drop-wise manner to a –65° C. solution of C2 (4.33 g, 14.3 mmol) in tetrahydrofuran (140 mL), at a rate that maintained the internal reaction temperature below –60° C. After completion of the addition, the reaction mixture was stirred at –60° C. for 3 hours, whereupon N-bromosuccinimide (3.82 g, 21.5 mmol) was added, and the reaction mixture was allowed to warm to 18° C. and stir for 16 hours. It was then combined with a similar reaction carried out using C2 (3.00 g, 9.92 mmol), and partitioned between aqueous sodium bicarbonate solution (300 mL) and ethyl acetate. The aqueous layer was extracted with ethyl acetate (3×200 mL); the combined organic layers were washed with saturated aqueous sodium chloride solution (400 mL), dried over sodium sulfate, filtered, and concentrated in vacuo, affording a white-brown solid (9.24 g), which was used directly in the following step. By $^1$H NMR analysis, this material was an approximately 1:1 mixture of C6 and C2. $^1$H NMR (400 MHz, chloroform-d), C6 peaks only: δ 6.18 (s, 1H), 4.21-4.1 (m, 2H), 4.08-4.00 (m, 2H), 0.37 (d, J=0.9 Hz, 9H).

Step 2. Synthesis of 2-(3-bromo-5-fluorothieno[3,2-b]thiophen-2-yl)-1,3-dioxolane (C7)

To a solution of C6 and C2 (from the previous step; 9.24 g, <24.2 mmol) in tetrahydrofuran (120 mL) and water (0.437 mL, 24.2 mmol) was added tetrabutylammonium fluoride (1 M solution in tetrahydrofuran; 36.4 mL, 36.4 mmol). After the reaction mixture had been stirred at 20° C. for 1 hour, it was poured into saturated aqueous sodium bicarbonate solution (70 mL) at 0° C., and the resulting mixture was stirred, then extracted with ethyl acetate (3×60 mL). The combined organic layers were washed with saturated aqueous sodium chloride solution, dried over sodium sulfate, filtered, and concentrated in vacuo to provide C7 (7.49 g) as a brown solid. This material was used directly in the following step.

Step 3. Synthesis of 3-bromo-5-fluorothieno[3,2-b]thiophene-2-carbaldehyde (C8)

To a solution of C7 (from the previous step; 7.49 g, <24.2 mmol) in tetrahydrofuran (120 mL) was added hydrochloric acid (2 M; 12 mL) in a drop-wise manner. The reaction mixture was stirred at 40° C. for 2 hours, whereupon it was diluted with water (100 mL) and extracted with ethyl acetate (3×80 mL). The combined organic layers were washed with saturated aqueous sodium chloride solution, dried over sodium sulfate, filtered, concentrated in vacuo, and purified via silica gel chromatography (Gradient: 0% to 20% ethyl acetate in petroleum ether) to afford C8 as a white solid. Yield: 1.35 g, 5.09 mmol, 21% over three steps. $^1$H NMR (400 MHz, chloroform-d) δ 9.99 (s, 1H), 6.91 (d, J=1.2 Hz, 1H).

Step 4. Synthesis of 3-bromo-5-fluorothieno[3,2-b]thiophene-2-carboxylic acid (2)

A solution of C8 (1.35 g, 5.09 mol) in acetonitrile (20 mL) was cooled to 0° C. A solution of sodium dihydrogen phosphate (794 mg, 6.62 mmol) in water (1 mL) and an aqueous solution of hydrogen peroxide (30%; 2.6 mL, 25 mmol) were added, followed by addition of a solution of sodium chlorite (599 mg, 6.62 mmol) in water (3 mL) over 5 minutes. The resulting biphasic reaction mixture was vigorously stirred at 0° C. for 2 hours, then at 18° C. for 16 hours, whereupon it was poured into aqueous sodium sulfite solution (20 mL). The resulting mixture was stirred for 10 minutes, and then the pH of the mixture was adjusted to approximately 1. The mixture was extracted with ethyl acetate (3×40 mL), and the combined organic layers were washed with saturated aqueous sodium chloride solution (50 mL), dried over sodium sulfate, filtrated, and concentrated in vacuo. The residue was stirred in petroleum ether (10 mL) for 30 minutes, and then filtered, providing 3-bromo-5-fluorothieno[3,2-b]thiophene-2-carboxylic acid as a white solid. Yield: 964 mg, 3.43 mmol, 67%. LCMS m/z 234.9 (bromine isotope pattern observed) [(M−CO$_2$)+H]$^+$. $^1$H NMR (400 MHz, DMSO-d6) δ 13.7-12.9 (br s, 1H), 7.45 (d, J=1.8 Hz, 1H).

Example 3

3-(Difluoromethyl)-5-fluorothieno[3,2-b]thiophene-2-carboxylic acid (3)

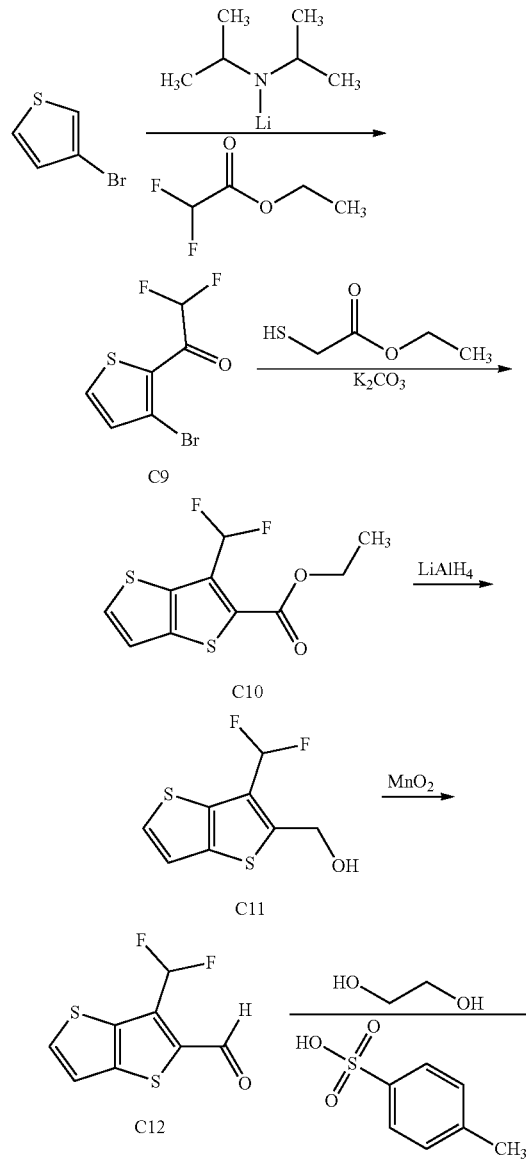

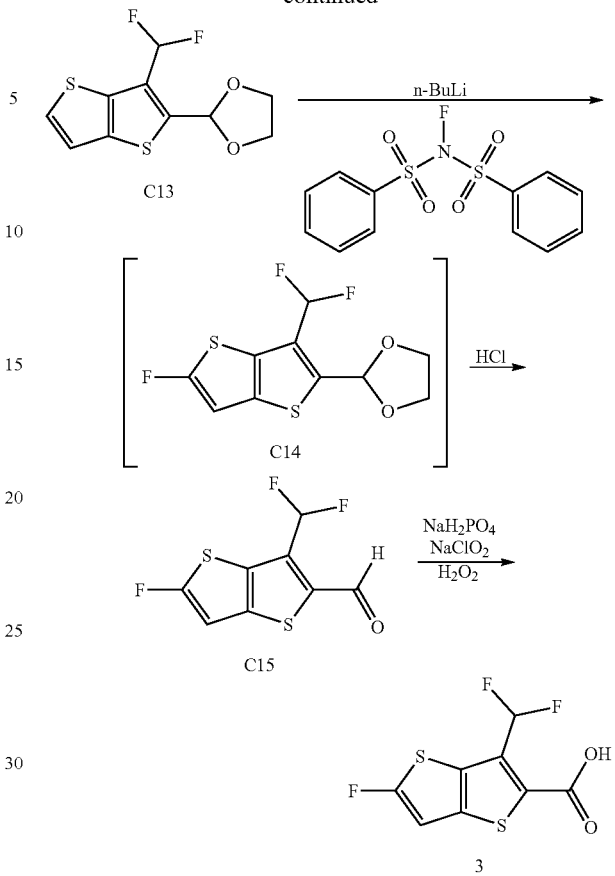

Step 1. Synthesis of 1-(3-bromo-2-thiophenyl)-2,2-difluoroethanone (C9)

Lithium diisopropylamide (2.0 M; 73.6 mL, 147 mmol) was added drop-wise to a −70° C. solution of 3-bromothiophene (20.0 g, 123 mmol) in tetrahydrofuran (240 mL). After the reaction mixture had been stirred at −70° C. for 1 hour, ethyl difluoroacetate (14.8 mL, 141 mmol) was added drop-wise at −78° C. Stirring was continued at that temperature for one hour, whereupon the reaction mixture was slowly warmed to 15° C. and stirred at 15° C. overnight. Hydrochloric acid (1 M; 500 mL) was added, followed by ethyl acetate (500 mL); the organic layer was washed with saturated aqueous sodium chloride solution (500 mL) and filtered, and the filtrate was concentrated in vacuo to afford C9 (29.6 g) as a brown oil. This material was used directly in the following step. $^1$H NMR (400 MHz, methanol-d4) δ 7.51-7.45 (m, 1H), 7.04-6.99 (m, 1H), 6.07 (t, $J_{HF}$=55.7 Hz, 1H).

Step 2. Synthesis of ethyl 3-(difluoromethyl)thieno[3,2-b]thiophene-2-carboxylate (C10)

Ethyl mercaptoacetate (13.4 mL, 122 mmol) was added in a drop-wise manner to a 65° C. mixture of C9 (from the previous step; 29.6 g, ≤123 mmol) and potassium carbonate (76.3 g, 552 mmol) in N,N-dimethylformamide. After the reaction mixture had been stirred at 65° C. for 16 hours, it was poured into water (400 mL) and extracted with ethyl acetate (2×400 mL). The combined organic layers were washed sequentially with aqueous lithium chloride solution (3%; 3×400 mL) and saturated aqueous sodium chloride solution (2×400 mL), dried over sodium sulfate, filtered, and concentrated in vacuo. Chromatography on silica gel (Gradient: 0% to 10% ethyl acetate in petroleum ether) provided C10 as a yellow solid. Yield: 22.6 g, 86.2 mmol, 70% over 2 steps. $^1$H NMR (400 MHz, chloroform-d) δ 7.67 (d, J=5.3 Hz, 1H), 7.56 (t, $J_{HF}$=55.1 Hz, 1H), 7.29 (br d, J=5.4 Hz, 1H), 4.41 (q, J=7.1 Hz, 2H), 1.42 (t, J=7.1 Hz, 3H).

Step 3. Synthesis of [3-(difluoromethyl)thieno[3,2-b]thiophen-2-yl]methanol (C11)

A mixture of lithium aluminum hydride (6.40 g, 169 mmol) in tetrahydrofuran (500 mL) was added drop-wise to a 0° C. solution of C10 (22.1 g, 84.3 mmol) in tetrahydrofuran (300 mL), and the reaction mixture was stirred for 30 minutes at 0° C., then at 20° C. for 2 hours. it was then cooled to 0° C. and treated sequentially with water (6.4 mL), aqueous sodium hydroxide solution (15%; 6.4 mL), and water (3×6.4 mL). After filtration of the resulting mixture, the filter cake was stirred with ethyl acetate (3×40 mL) for 10 minutes, and filtered; the combined filtrates were concentrated in vacuo to afford C11 as a yellow solid. This material was taken directly to the following step. $^1$H NMR (400 MHz, chloroform-d) δ 7.43 (d, J=5.3 Hz, 1H), 7.24 (d, J=5.3 Hz, 1H), 6.98 (t, $J_{HF}$=55.6 Hz, 1H), 4.95 (br s, 2H), 2.10 (br s, 1H).

Step 4. Synthesis of 3-(difluoromethyl)thieno[3,2-b]thiophene-2-carbaldehyde (C12)

To a solution of C11 (from the previous step; 584.3 mmol) in dichloromethane (420 mL) was added manganese(IV) oxide (73.3 g, 843 mmol). After the reaction mixture had been stirred at 20° C. for 16 hours, it was filtered; the filtrate was concentrated in vacuo to provide C12 as a yellow solid. Yield: 14.0 g, 64.1 mmol, 76% over 2 steps. $^1$H NMR (400 MHz, chloroform-d) δ 10.08 (s, 1H), 7.76 (d, J=5.3 Hz, 1H), 7.36 (d, J=5.3 Hz, 1H), 7.34 (t, $J_{HF}$=55.0 Hz, 1H).

Step 5. Synthesis of 2-[3-(difluoromethyl)thieno[3,2-b]thiophen-2-yl]-1,3-dioxolane (C13)

1,2-Ethanediol (17.8 mL, 319 mmol) and p-toluenesulfonic acid monohydrate (122 mg, 0.641 mmol) were added to a solution of C12 (14.0 g, 64.1 mmol) in toluene (100 mL), and the reaction mixture was heated at reflux (130° C.) overnight, while water generated from the reaction was removed using a Dean-Stark trap. After the reaction mixture had cooled to 15° C., saturated aqueous sodium bicarbonate solution (200 mL) was added, and the mixture was extracted with ethyl acetate (2×200 mL). The combined organic layers were washed sequentially with saturated aqueous sodium bicarbonate solution (2×200 mL), water (2×200 mL), and saturated aqueous sodium chloride solution (2×200 mL), then dried over sodium sulfate, filtered, and concentrated in vacuo to provide a yellow oil (16.0 g). A portion of this oil (15 g) was subjected to purification via silica gel chromatography (Gradient: 0% to 20% ethyl acetate in petroleum ether) to afford C13 (14.3 g, 54.5 mmol) as a yellow oil. Adjusted yield: 15.2 g, 58.0 mmol, 90%. LCMS m/z 263.0 [M+H]$^+$. $^1$H NMR (400 MHz, chloroform-d) δ 7.45 (d, J=5.3 Hz, 1H), 7.24 (d, J=5.3 Hz, 1H), 7.09 (t, $J_{HF}$=55.4 Hz, 1H), 6.35-6.32 (m, 1H), 4.17-4.03 (m, 4H).

Step 6. Synthesis of 2-[3-(difluoromethyl)-5-fluoro-thieno[3,2-b]thiophen-2-yl]-1,3-dioxolane (C14)

n-Butyllithium (2.5 M solution; 3.66 mL, 9.15 mmol) was added in a drop-wise manner to a −70° C. solution of C13 (2.00 g, 7.62 mmol) in tetrahydrofuran (30 mL). After the reaction mixture had been stirred at −70° C. for 4 hours, a solution of N-fluoro-N-(phenylsulfonyl)benzenesulfonamide (2.89 g, 9.16 mmol) in tetrahydrofuran (10 mL) was added, and the reaction mixture was warmed to 15° C. and stirred at 15° C. for 16 hours. Saturated aqueous sodium bicarbonate solution (50 mL) was added, and the resulting mixture was extracted with ethyl acetate (3×50 mL); the combined organic layers were washed with saturated aqueous sodium chloride solution (100 mL), dried over sodium sulfate, filtered, and concentrated in vacuo to provide C14, which was progressed directly to the following step.

Step 7. Synthesis of 3-(difluoromethyl)-5-fluorothieno[3,2-b]thiophene-2-carbaldehyde (C15)

To a solution of C14 (from the previous step; 57.62 mmol) in tetrahydrofuran (20 mL) was added hydrochloric acid (2 M; 3.82 mL, 7.64 mmol), and the reaction mixture was stirred at 40° C. for 2 hours. It was then concentrated in vacuo to remove tetrahydrofuran, and diluted with water (50 mL). The resulting mixture was extracted with ethyl acetate (3×50 mL), and the combined organic layers were washed with saturated aqueous sodium chloride solution (100 mL), dried over sodium sulfate, filtered, concentrated in vacuo, and purified via silica gel chromatography (Gradient: 0% to 20% ethyl acetate in petroleum ether) to provide a yellow solid (756 mg). By $^1$H NMR analysis, this material was an equimolar mixture of C15 and C12, which was progressed directly to the following step. $^1$H NMR (400 MHz, chloroform-d), peaks for C15 only: δ 10.01 (s, 1H), 7.31 (t, $J_{HF}$=55.0 Hz, 1H), 6.91-6.89 (m, 1H).

Step 8. Synthesis of 3-(difluoromethyl)-5-fluorothieno[3,2-b]thiophene-2-carboxylic acid (3)

A solution of C15 (from the previous step, containing C12 as well; 756 mg) and C15 [461 mg; derived from C13 (2.0 g, 7.6 mmol) through similar chemistry] in acetonitrile (20 mL) was cooled to 0° C. After a solution of sodium dihydrogen phosphate (86.5 mg, 0.721 mmol) in water (1 mL) and an aqueous solution of hydrogen peroxide (30%; 2.63 mL, 23 mmol) had been added, a solution of sodium chlorite (303 mg, 3.35 mmol) in water (3 mL) was added over 5 minutes. The resulting two-phase reaction mixture was vigorously stirred for 2 hours at 0° C., and then at room temperature (15° C.) for 16 hours. It was subsequently cooled to 0° C., treated with sodium chlorite (303 mg, 3.35 mmol) and sodium dihydrogen phosphate (618 mg, 5.15 mmol), and stirred at 15° C. overnight. The reaction mixture was then cooled to 10° C., quenched via addition of an aqueous solution of sodium sulfite (20 mL), and poured into an aqueous solution of sodium sulfite (100 mL). Water (20 mL) was added, and the resulting mixture was adjusted to pH 1 by addition of 5 M hydrochloric acid; this provided a suspension, which was filtered. The collected solid was washed with water and purified via reversed-phase HPLC (Column: YMC-Actus Triart C18, 5 μm; Mobile phase A: water containing 0.225% formic acid; Mobile phase B: acetonitrile; Gradient: 48% to 68% B) to provide 3-(difluoromethyl)-5-fluorothieno[3,2-b]thiophene-2-carboxylic acid as a white solid. Combined yield: 439 mg, 1.74 mmol, 11% over 3 steps. LCMS m/z 251.0 [M−H]⁻. ¹H NMR (400 MHz, DMSO-d6) δ 14.3-13.9 (br s, 1H), 7.63 (t, $J_{HF}$=54.9 Hz, 1H), 7.43 (br s, 1H).

Example 4

5,6-Difluorothieno[3,2-b]thiophene-2-carboxylic acid (4)

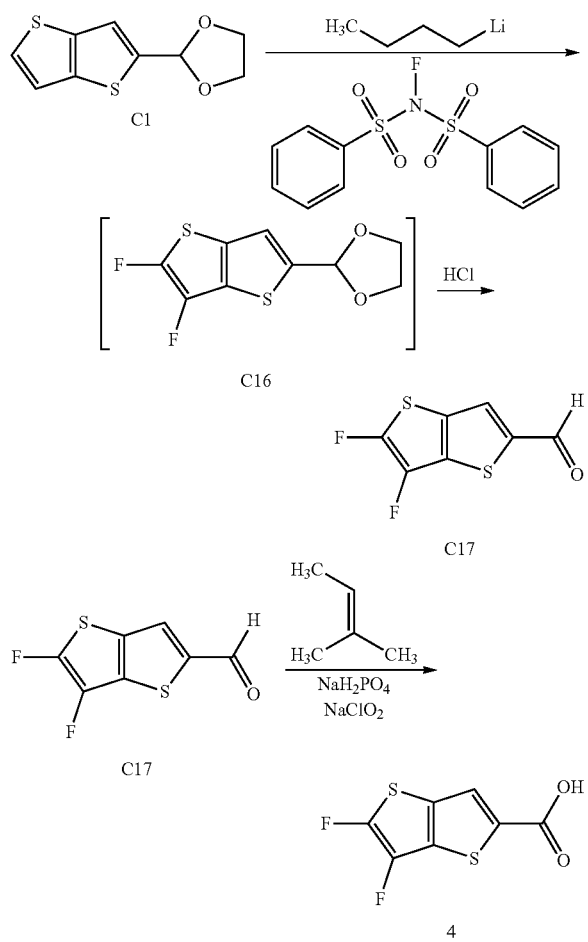

Step 1. Synthesis of 5,6-difluorothieno[3,2-b]thiophene-2-carbaldehyde (C17)

To a −78° C. solution of C1 (4.05 g, 19.1 mmol) in tetrahydrofuran (191 mL) was added n-butyllithium (2.5 M in hexanes, 9.92 mL, 24.8 mmol), in a drop-wise manner. After the reaction mixture had been stirred at −78° C. for 2 hours, a solution of N-fluoro-N-(phenylsulfonyl)benzenesulfonamide (7.82 g, 24.8 mmol) in tetrahydrofuran (20 mL) was added drop-wise. Stirring was continued at −78° C. for 30 minutes, whereupon the reaction mixture was allowed to slowly warm to room temperature. After 3 hours, it was cooled to −78° C. and treated drop-wise with n-butyllithium (2.5 M in hexanes; 11.4 mL, 28.5 mmol), then stirred at −78° C. for 1 hour. A solution of N-fluoro-N(phenylsulfonyl) benzenesulfonamide (10.2 g, 32.3 mmol) in tetrahydrofuran (30 mL) was again added drop-wise, and the reaction mixture was allowed to warm to room temperature and stir overnight. GCMS analysis at this point indicated a mixture of C16 {2-(5,6-difluorothieno[3,2-b]thiophen-2-yl)-1,3-dioxolane; GCMS m/z 248.0 [M]⁺} and its mono-fluoro analogue, presumed to be 2-(5-fluorothieno[3,2-b]thiophen-2-yl)-1,3-dioxolane (GCMS m/z 230.0 [M]⁺). Water (19 mL) was added, followed by a solution of hydrogen chloride in 1,4-dioxane (4.0 M; 28.6 mL, 114 mmol); stirring was continued at room temperature for 30 minutes, whereupon the reaction mixture was diluted with water and extracted with ethyl acetate. The combined organic layers were dried over sodium sulfate, filtered, concentrated in vacuo, and purified using silica gel chromatography (Gradient: 0% to 100% ethyl acetate in heptane) to afford C17 as an orange oil (3.06 g). This material was used directly in the following step. LCMS m/z 204.8 [M+H]⁺. LCMS also indicated the presence of a mono-fluoro analogue, presumed to be 5-fluorothieno[3,2-b]thiophene-2-carbaldehyde: LCMS m/z 186.9 [M+H]⁺.

Step 2. Synthesis of 5,6-difluorothieno[3,2-b]thiophene-2-carboxylic acid (4)

A solution of C17 (from the previous step, 3.06 g) in tetrahydrofuran (100 mL), water (25 mL), and 2-methyl-2-butene (25 mL) was treated sequentially with sodium dihydrogen phosphate (8.99 g, 74.9 mmol) and sodium chlorite (6.78 g, 75.0 mmol). After the reaction mixture had been stirred at room temperature for 1 hour, it was diluted with water and extracted with ethyl acetate. The combined organic layers were dried over sodium sulfate, filtered, concentrated in vacuo, and subjected to silica gel chromatography (Gradient: 0% to 20% methanol in dichloromethane), then purified via reversed-phase chromatography on a C18 column [Gradient: 25% to 100% water (containing 0.01% trifluoroacetic acid) in acetonitrile (containing 0.01% trifluoroacetic acid)]. The resulting solid was stirred in water, filtered, and washed with water, then dissolved in ethanol and filtered; concentration of the filtrate in vacuo provided a solid, which was then precipitated from an ethanol solution upon cooling to provide 5,6-difluorothieno [3,2-b]thiophene-2-carboxylic acid as a white solid. Yield: 1.19 g, 5.40 mmol, 28% over 2 steps. LCMS m/z 219.1 [M−H]⁻. ¹H NMR (400 MHz, DMSO-d6) δ 13.6-13.5 (br s, 1H), 8.12 (d, J=2.1 Hz, 1H).

Example 5

3,5-Difluorothieno[3,2-b]thiophene-2-carboxylic acid (5)

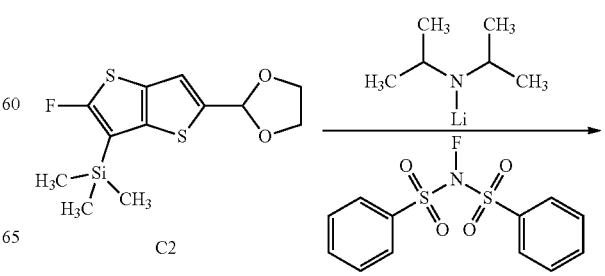

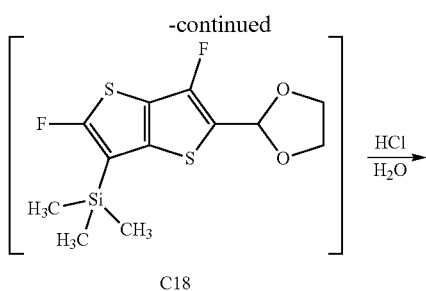

C18

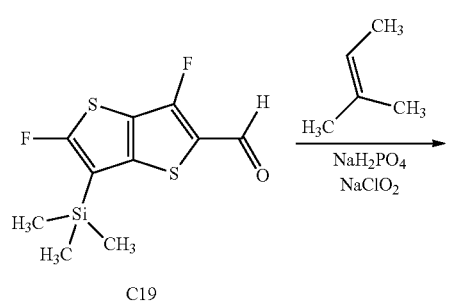

C19

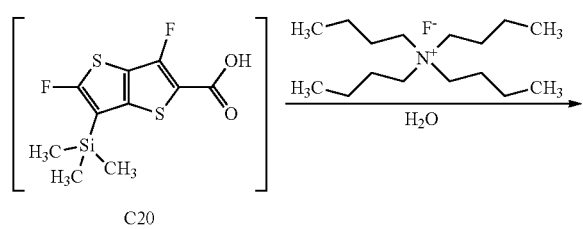

C20

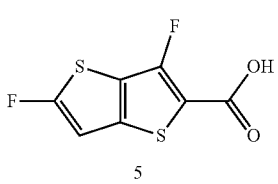

5

Step 1. Synthesis of 3,5-difluoro-6-(trimethylsilyl)thieno[3,2-b]thiophene-2-carbaldehyde (C19)

Lithium diisopropylamide (2.0 M solution in tetrahydrofuran/heptane/ethylbenzene; 15.4 mL, 30.8 mmol) was added in a drop-wise manner to a −78° C. solution of C2 (6.22 g, 20.6 mmol) in tetrahydrofuran (137 mL). After the reaction mixture had been stirred at −78° C. for 3 hours, a solution of N-fluoro-N(phenylsulfonyl)benzenesulfonamide (13.0 g, 41.2 mmol) in tetrahydrofuran (8 mL) was added drop-wise, and stirring was continued for 30 minutes at −78° C. The reaction mixture was then allowed to slowly warm to room temperature and stir overnight, whereupon it was diluted with water (20 mL) and treated with a solution of hydrogen chloride in 1,4-dioxane (4.0 M; 20.6 mL, 82.4 mmol) to hydrolyze the presumed intermediate C18 {[5-(1,3-dioxolan-2-yl)-2,6-difluorothieno[3,2-b]thiophen-3-yl](trimethyl)silane}. After the reaction mixture had stirred for 2 hours at room temperature, it was diluted with water and extracted with diethyl ether. The combined organic layers were dried over sodium sulfate, filtered, concentrated in vacuo, and purified using silica gel chromatography (Gradient: 0% to 80% ethyl acetate in heptane) to afford C19 as a yellow oil that solidified overtime to an orange solid. Yield: 1.48 g, 5.35 mmol, 26%. LCMS m/z 277.1 [M+H]$^+$. $^1$H NMR (400 MHz, chloroform-d) 10.05 (s, 1H), 0.41 (d, J=0.9 Hz, 9H).

Step 2. Synthesis of 3,5-difluorothieno[3,2-b]thiophene-2-carboxylic acid (5)

Sodium dihydrogen phosphate (3.22 g, 26.8 mmol) and sodium chlorite (2.43 g, 26.9 mmol) were added to a solution of C19 (1.48 g, 5.35 mmol) in tetrahydrofuran (45 mL), water (9 mL), and 2-methyl-2-butene (9 mL), whereupon the reaction mixture was stirred at room temperature for 1 hour. It was then diluted with water and extracted with ethyl acetate; the combined organic layers were dried over sodium sulfate, filtered, and concentrated in vacuo. The resulting solid {C20; 3,5-difluoro-6-(trimethylsilyl)thieno[3,2-b]thiophene-2-carboxylic acid, LCMS m/z 293.0 [M+H]$^+$} was dissolved in tetrahydrofuran (45 mL) and treated sequentially with water (0.483 mL, 26.8 mmol) and a solution of tetrabutylammonium fluoride in tetrahydrofuran (1.0 M; 6.44 mL, 6.44 mmol). After 5 minutes, LCMS analysis indicated that the reaction was complete; the reaction mixture was treated with hydrochloric acid (1 M; 10.7 mL, 10.7 mmol), diluted with water, and extracted with ethyl acetate. After the combined organic layers had been dried over sodium sulfate, they were filtered, concentrated in vacuo, and subjected to silica gel chromatography (Gradient: 0% to 20% methanol in dichloromethane), followed by reversed-phase chromatography using a C18 column [Gradient: 10% to 100% water (containing 0.01% trifluoroacetic acid) in acetonitrile (containing 0.01% trifluoroacetic acid)]. Upon removal of organic solvents from the product-containing fractions in vacuo, a solid precipitated. The resulting aqueous mixture was extracted with ethyl acetate, and the combined organic layers were dried over sodium sulfate, filtered, and concentrated in vacuo. The resulting solid was triturated with diethyl ether and heptane, then purified using silica gel chromatography (Gradient: 0% to 100% ethyl acetate in heptane, then 0% to 30% methanol in ethyl acetate) followed by reversed-phase chromatography on a C18 column (Gradient: 10% to 100% water in acetonitrile). The precipitated solid was collected via filtration after removing organic solvents in vacuo from the appropriate fractions; it was then washed with water, dissolved in ethanol and filtered. After the filtrate had been concentrated in vacuo, the residue was triturated with ethanol and heptane to provide 3,5-difluorothieno[3,2-b]thiophene-2-carboxylic acid as a white solid. Yield: 718 mg, 3.26 mmol, 61%. LCMS m/z 175.1 [(M−CO$_2$)—H]$^-$. $^1$H NMR (400 MHz, DMSO-d6) δ 13.6-13.5 (br s, 1H), 7.39 (dd, J=1.7, 1.7 Hz, 1H).

TABLE 1

Method of Synthesis, Structure, Compound Name, and Characterization Data for Examples 6-16, BT2, and BT2F.

| Example Number | Method of synthesis; Non-commercial starting materials; literature reference | Structure | Compound Name | $^1$H NMR (400 MHz, DMSO-$d_6$) δ; Mass spectrum, observed ion m/z [M + H]$^+$ or HPLC retention time; Mass spectrum m/z [M + H]$^+$ (unless otherwise indicated) |
|---|---|---|---|---|
| 6 | Footnote 1 | 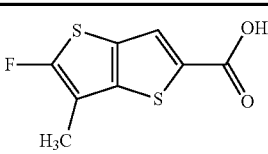 | 5-fluoro-6-methylthieno[3,2-b]thiophene-2-carboxylic acid | 13.30-13.15 (br s, 1H), 8.08 (s, 1H), 2.24 (d, J = 2.0 Hz, 3H); LCMS m/z 215.0 [M − H]$^-$ |
| 7 | Cl[2] | 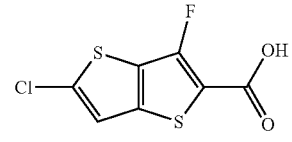 [SMILES: O=C(O)c1sc2cc(Cl)sc2c1F] | 5-chloro-3-fluorothieno[3,2-b]thiophene-2-carboxylic acid | 13.7-13.6 (br s, 1H), 7.70 (d, J = 1.9 Hz, 1H); LCMS m/z 191.1 (chorine isotope pattern observed) [(M − CO$_2$) − H]$^-$ |
| 8 | 4[3] | 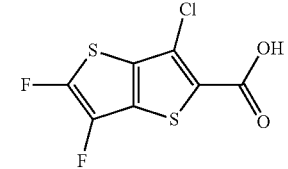 [SMILES: O=C(O)c1sc2c(F)c(F)sc2c1Cl] | 3-chloro-5,6-difluorothieno[3,2-b]thiophene-2-carboxylic acid | 14 (br s, 1H, assumed); LCMS m/z 209.1 (chorine isotope pattern observed) [(M − CO$_2$) − H]$^-$ |
| 9 | C2[4] | 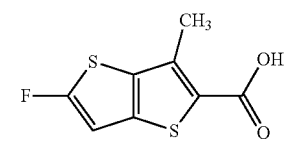 | 5-fluoro-3-methylthieno[3,2-b]thiophene-2-carboxylic acid | 13.2-13.1 (br s, 1H), 7.33 (d, J = 1.8 Hz, 1H), 2.56 (s, 3H); LCMS m/z 215.1 [M − H]$^-$ |
| 10 | Footnote 5 | 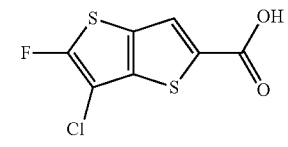 [SMILES: O=C(O)c1cc2sc(F)c(Cl)c2s1] | 6-chloro-5-fluorothieno[3,2-b]thiophene-2-carboxylic acid | 13.6-13.5 (br s, 1H), 8.15 (s, 1H); LCMS m/z 235.0 (chlorine isotope pattern observed) [M − H]$^-$ |
| 11 | C10[6] | 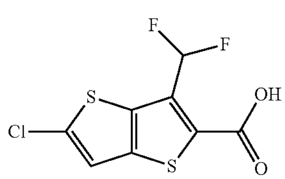 [SMILES: O=C(O)c1sc2cc(Cl)sc2c1C(F)F] | 5-chloro-3-(difluoromethyl)thieno[3,2-b]thiophene-2-carboxylic acid | 14.5-14.0 (br s, 1H), 7.75 (s, 1H), 7.62 (t, J$_{HF}$ = 54.8 Hz, 1H); 269.0 (chlorine isotope pattern observed) |
| 12 | C1[7] | 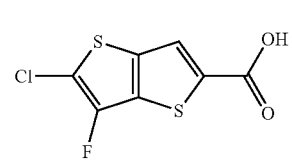 [SMILES: O=C(O)c1cc2sc(Cl)c(F)c2s1] | 5-chloro-6-fluorothieno[3,2-b]thiophene-2-carboxylic acid | $^1$H NMR (400 MHz, methanol-$d_4$) δ 7.96 (d, J = 2.2 Hz, 1H); LCMS m/z 191.0 (chlorine isotope pattern observed) [(M − CO$_2$) − H]$^-$ |
| 13 | Footnote 8 | 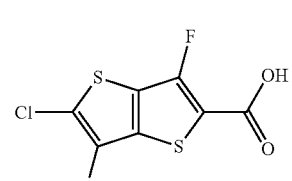 | 5-chloro-3,6-difluorothieno[3,2-b]thiophene-2-carboxylic acid | 2.89 minutes[9]; 255.2 (chlorine isotope pattern observed) |

TABLE 1-continued

Method of Synthesis, Structure, Compound Name, and Characterization Data for Examples 6-16, BT2, and BT2F.

| Example Number | Method of synthesis; Non-commercial starting materials; literature reference | Structure | Compound Name | $^1$H NMR (400 MHz, DMSO-$d_6$) δ; Mass spectrum, observed ion m/z [M + H]$^+$ or HPLC retention time; Mass spectrum m/z [M + H]$^+$ (unless otherwise indicated) |
|---|---|---|---|---|
| 14 | Footnote 10 | 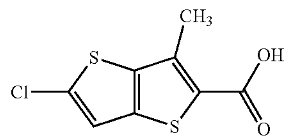 | 5-chloro-3-methylthieno[3,2-b]thiophene-2-carboxylic acid | $^1$H NMR (600 MHz, methanol-$d_4$) δ 7.34 (s, 1H), 2.61 (s, 3H); LCMS m/z 230.9 (chlorine isotope pattern observed) [M − H]$^−$ |
| 15 | Footnote 11 | 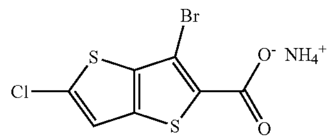 [SMILES: O=C([O-])c1sc2cc(Cl)sc2c1Br ; [NH4+]] | ammonium 3-bromo-5-chlorothieno[3,2-b]thiophene-2-carboxylate | 3.08 minutes$^9$; 297.1 (bromo chloro isotope pattern observed) |
| 16 | Footnote 12 | 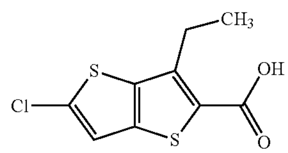 | 5-chloro-3-ethylthieno[3,2-b]thiophene-2-carboxylic acid | 7.65 (s, 1H), 3.08 (q, J = 7.6 Hz, 2H), 1.21 (t, J = 7.6 Hz, 3H); LCMS m/z 245.0 (chlorine isotope pattern observed) [M − H]$^−$ |
| BT2 | Footnote 13 | 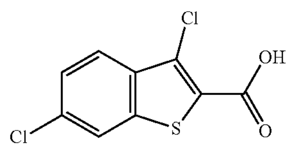 [SMILES: O=C(O)c1sc2cc(Cl)ccc2c1Cl] | 3,6-dichloro-1-benzothiophene-2-carboxylic acid | 8.33 (d, J = 1.9 Hz, 1H), 7.94 (d, J = 8.7 Hz, 1H), 7.63 (dd, J = 8.7, 2.0 Hz, 1H); LCMS m/z 201.2 (dichloro isotope pattern observed) [(M − CO$_2$) − H]$^−$ |
| BT2F | Footnote 13 | 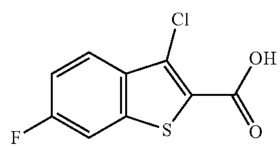 [SMILES: O=C(O)c1sc2cc(F)ccc2c1Cl] | 3-chloro-6-fluoro-1-benzothiophene-2-carboxylic acid | $^1$H NMR (400 MHz, methanol-$d_4$) δ 7.99 (dd, J = 9.0, 5.1 Hz, 1H), 7.73 (dd, J = 8.8, 2.3 Hz, 1H), 7.35 (ddd, J = 9.0, 9.0, 2.4 Hz, 1H); 231.1 (chlorine isotope pattern observed) |

1. Treatment of 5-fluorothieno[3,2-b]thiophene-2-carboxylic acid (see Gronowitz, S.; Herslf, M.; Svenson, R.; Bondesson, G.; Magnusson, 0.; Stjernstrom, N. E. *Acta Pharm. Suec.* 1978, 15, 368-381) with 2 equivalents of lithium diisopropylamide, followed by iodomethane, afforded Example 6.

2. Treatment of C1 with n-butyllithium and trimethylsilyl chloride provided [5-(1,3-dioxolan-2-yl)thieno[3,2-b]thiophen-2-yl](trimethyl)silane, which was reacted with n-butyllithium and N-fluoro-N-(phenylsulfonyl)benzenesulfonamide, followed by tetrabutylammonium fluoride, to afford 2-(3-fluorothieno[3,2-b]thiophen-2-yl)-1,3-dioxolane. This material was reacted with n-butyllithium and hexachloroethane to provide 2-(5-chloro-3-fluorothieno[3,2-b]thiophen-2-yl)-1,3-dioxolane, which was converted to Example 7 using the chemistry described in Example 4 to synthesize 4 from C16.

3. Reaction of 4 with 3 equivalents of lithium diisopropylamide, followed by hexachloroethane, provided Example 8.

4. Reaction of C2 with lithium diisopropylamide and iodomethane, followed by desilylation with tetrabutylammonium fluoride, afforded 2-(5-fluoro-3-methylthieno[3,2-b]thiophen-2-yl)-1,3-dioxolane. This material was converted to Example 9 using the method described for synthesis of 4 from C16 in Example 4.

5. Treatment of 5-fluorothieno[3,2-b]thiophene-2-carboxylic acid (see Gronowitz, S.; Herslöf, M.; Svenson, R.; Bondesson, G.; Magnusson, O.; Stjernström, N. E. *Acta Pharm. Suec.* 1978, 15, 368-381) with 2 equivalents of lithium diisopropylamide, followed by N-chlorosuccinimide, provided Example 10.

6. Chlorination of C10 with N-chlorosuccinimide afforded ethyl 5-chloro-3-(difluoromethyl)thieno[3,2-b]thiophene-2-carboxylate, which was subjected to ester hydrolysis with sodium hydroxide to provide Example 11.

7. Reaction of C1 with lithium diisopropylamide and hexachloroethane provided 2-(5-chlorothieno[3,2-b]thiophen-2-yl)-1,3-dioxolane, which was then fluorinated using nbutyllithium and N-fluoro-N-(phenylsulfonyl)benzenesulfonamide. The resulting 2-(5-chloro-6-fluorothieno[3,2-b]thiophen-2-yl)-1,3-dioxolane was converted to Example 12 using the chemistry described in Example 4 to synthesize 4 from C16.

8. 2-(5-Chloro-3-fluorothieno[3,2-b]thiophen-2-yl)-1,3-dioxolane (see footnote 2) was fluorinated with lithium diisopropylamide and N-fluoro-N(phenylsulfonyl)benzenesulfonamide. The resulting 2-(5-chloro-3,6-difluorothieno

[3,2-b]thiophen-2-yl)-1,3-dioxolane was converted to Example 13 using the chemistry described in Example 4 to synthesize 4 from C16.

9. Conditions for analytical HPLC. Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

10. 3-Methylthieno[3,2-b]thiophene-2-carboxylic acid (see Deng, H.; Fang, Y.; He, M.; Hu, H.; Niu, W.; Sun, H. WO 2012012278, Jan. 26, 2012) was chlorinated using N-chlorosuccinimide to afford Example 14.

11. Reaction of 3-bromothiophene-2-carbonitrile with ethyl mercaptoacetate in the presence of potassium carbonate and 18-crown-6 (1,4,7,10,13,16-hexaoxacyclooctadecane) provided ethyl [(2-cyanothiophen-3-yl)thio]acetate. Cyclization with lithium bis(trimethylsilyl)amide afforded ethyl 3-aminothieno[3,2-b]thiophene-2-carboxylate, which was treated with 2-methyl-2-nitropropane and copper(II) bromide, and then subjected to ester hydrolysis with sodium hydroxide, providing 3-bromothieno[3,2-b]thiophene-2-carboxylic acid. Reaction with N-chlorosuccinimide afforded Example 15.

12. Reaction of lithium diisopropylamide with 2,5-dibromothiophene was followed by addition of N-methoxy-N-methylpropanamide. The resulting 1-(3,5-dibromo-2-thiophenyl)-1-propanone was converted to ethyl 5-bromo-3-ethylthieno[3,2-b]thiophene-2-carboxylate with ethyl mercaptoacetate in the presence of potassium carbonate and 18-crown-6. Ester hydrolysis via treatment with lithium hydroxide was then followed by metal-halogen exchange with n-butyllithium and reaction with N-chlorosuccinimide to afford Example 16.

13. BT2 and BT2F synthesis is described in Tso, S.-C.; Gui, W.-J.; Wu, C.-Y.; Chuang, J. L.; Qi, X.; Skvorak, K. J.; Dorko, K.; Wallace, A. L.; Morlock, L. K.; Lee, B. H.; Hutson, S. M.; Strom, S. C.; Williams, N. S.; Tambar, U. K.; Wynn, R. M.; Chuang, D. T. *J. Biol. Chem.* 2014, 289, 20583-20593.

The following protocols may of course be varied by those skilled in the art.

Protein Generation

BCKDK protein was generated using a pET vector containing from N- to C-terminus: 6×His, MBP, a TEV protease site (ENLYFQG), a biotin acceptor peptide (GLNDIFEAQKIEWHE), and human BCKDK (residues 31-412 of the protein pre-processing). Protein was co-expressed with GroEL-GroES in BL21(DE3) *E. coli* in LB media, and protein production was induced with 0.5 mM IPTG and 0.5 mg/mL L-arabinose at an $OD_{600}$ of 1 and grown for 16 h at 26° C. Bacteria were lysed using a Microfluidizer in 100 mM potassium phosphate pH 7.5, 500 mM NaCl, 0.1 mM EDTA, 1% Tween-20, 0.25% Triton X-100, 10% glycerol, 1 mM DTT, and protease inhibitors. MBP-tagged protein was purified by affinity chromatography using amylose resin, and MBP was removed from BCKDK by TEV protease incubation followed by gel filtration chromatography in 50 mM HEPES pH 7.5, 500 mM NaCl, 300 mM L-Arginine, 2 mM $MgCl_2$, 1 mM DTT, and 10% glycerol.

A pET vector containing *E. coli* LpIA was expressed in BL21(DE3) *E. coli* in LB media, and protein production was induced with 0.75 mM IPTG at an $OD_{600}$ of 1 and grown for 16 h at 30° C. Bacteria were lysed using a Microfluidizer in 50 mM sodium phosphate buffer pH 7.5, 350 mM NaCl, 1.5 mM $MgCl_2$, and 1 mM DTT. LpIA protein was precipitated from clarified lysate with 1 M ammonium sulfate and further purified by gel filtration chromatography in 50 mM sodium phosphate pH 7.5, 350 mM NaCl, 1.5 mM $MgCl_2$, 1 mM DTT, and 10% glycerol.

The BCKDHE1α-E2 fusion substrate was cloned into a pET vector and contained from N- to C-terminus: the lipoyl binding domain of E2 (residues 62-160 pre-processing), a TEV protease site (LENLYFQG), residues 331-345 (pre-processing) from E1a, and 6×His (Tso, S. C. et al., J Biol Chem 2014, 289 (30), 20583-20593). The fusion substrate was expressed in BL21(DE3) *E. coli* in LB media, and protein production was induced with 0.75 mM IPTG at an $OD_{600}$ of 1 and grown for 16 h at 30° C. Bacteria were lysed using a Microfluidizer in 50 mM sodium phosphate pH 7.5, 350 mM NaCl, 10 mM imidazole, 10% glycerol, 1 mM DTT, and protease inhibitors. Fusion substrate was purified by Ni-NTA affinity chromatography followed gel filtration chromatography in 50 mM sodium phosphate pH 7.5, 350 mM NaCl, 1.5 mM $MgCl_2$, 1 mM DTT, and 10% glycerol. For lipoylation, fusion substrate was incubated with LpIA at a 10:1 (substrate:LpIA) ratio in 20 mM sodium phosphate pH 7.4, 6 mM $MgCl_2$, 4 mM ATP, 2 mM DTT, 3 mM DL-6,8-thioctic acid at 37° C. The reaction was monitored using an Agilent 6530 Q-TOF coupled to an Agilent 1290 UPLC. The final lipoylated fusion substrate was purified by gel filtration chromatography in 50 mM HEPES pH 7.5, 350 mM NaCl, 1.5 mM $MgCl_2$, 1 mM DTT, 10% glycerol.

In Vitro FRET

BCKDK activity was monitored by phosphorylation of a HIS-tagged fusion BCKDHE1α-E2 substrate protein as described above and was detected using a time resolved-fluorescence resonance energy transfer (TR-FRET) assay system. Compounds were spotted into a 384 well plate, and purified human BCKDK protein was added to the plated compound. After incubation, the LBD-linker-E1 phosphorylation sequence was added in the presence of 15 µM ATP. The reaction was terminated with EDTA. Phosphorylated substrate was recognized by the addition of rabbit anti-E1 phospho Ser293 antibodies (Bethyl Laboratories—A304-672A), and the TR-FRET signal was developed by addition of anti-HIS donor molecules (Europium; Perkin Elmer-AD0205, AD0110, AD0111) and anti-Rabbit acceptor molecules (Ulight; Perkin Elmer-TRF502D, TRF502M, TRF502R). Recognition of phosphorylated E1 brought donor and acceptor molecules into close proximity, and excitation at 320 nm caused energy transfer from the Europium donor to the Ulight acceptor dye, which in turn generated light at 665 nm. Signal intensity was proportional to the level of BCKDK-mediated substrate phosphorylation. Reactions were normalized to zero percent effect with DMSO and one hundred percent effect with 600 µM Radicicol, a known BCKDK inhibitor. $IC_{50}$ curves were generated using ABASE software (IDBS, Boston Mass.).

Phospho BCKDHA AlphaLISA

Prior to conducting the assay, BCKDH antibodies (Bethyl A303-790A) were biotinylated using the ChromaLink™ One-Shot Antibody Biotinylation Kit B-9007-009K and phospho Ser293 BCKDHA antibodies (Bethyl A304-672A) were directly conjugated to AlphaLISA Acceptor Beads (custom conjugation performed by Perkin Elmer's Lance/ Delfia Custom Services, Boston Mass.). Human skeletal myocytes (Gibco A11440) were plated in a 384 well plate at a density of 7500 live cells/well and grown in skeletal muscle growth media containing the media supplement and chick embryo extract (Promocell C-23060 and C-23160, MP92850145). After overnight incubation, media was removed, and BCKDK inhibitors were added in assay media (growth media diluted 10-fold in PBS). After 60 minutes, the media was removed, the cells were washed with PBS and lysed in 10 μL of buffer (Cell Signaling #9803) containing 2 nM biotinylated total BCKDH antibodies. Samples were incubated for 60 minutes, and 5 μL of AlphaLISA acceptor beads conjugated with phospho-S293 BCKDH antibodies were added 1× Alpha buffer. After a 60 minute incubation, 5 μL streptavidin donor beads (40 μg/μL) beads were added in 1× Alpha buffer while protecting from light. Fluorescence was emitted when the phospho and total BCKDH antibodies were within proximity, signifying phosphorylation of S293 BCKDH. Fluorescence was monitored on the Envision plate reader. The zero percent effect was determined from DMSO treatment and the maximal effect was assessed relative to the BCKDK inhibitor BT2. $IC_{50}$ curves were generated using ActivityBase software (IDBS, Boston Mass.).

In Table 2 assay data ($IC_{50}$s) are presented for the Examples below in accordance with the above-described assays (to two (2) significant figures as the geometric mean, based on the number of replicates tested (Number)).

TABLE 2

In Vitro FRET and Phospho BCKDHA AlphaLISA Data for Examples 1-16, BT2, and BT2F.

| Example Number | Compound Name | In Vitro FRET $IC_{50}$ (μM) | N | Phospho BCKDHA AlphaLISA $IC_{50}$ (μM) | N |
|---|---|---|---|---|---|
| 1 | 3-chloro-5-fluorothieno[3,2-b]thiophene-2-carboxylic acid | 0.11 | 18 | 0.72 | 7 |
| 2 | 3-bromo-5-fluorothieno[3,2-b]thiophene-2-carboxylic acid | 0.12 | 8 | 1.5 | 4 |
| 3 | 3-(difluoromethyl)-5-fluorothieno[3,2-b]thiophene-2-carboxylic acid | 0.065 | 8 | 1.8 | 4 |
| 4 | 5,6-difluorothieno[3,2-b]thiophene-2-carboxylic acid | 0.058 | 12 | 0.39 | 7 |
| 5 | 3,5-difluorothieno[3,2-b]thiophene-2-carboxylic acid | 0.14 | 11 | 0.41 | 5 |
| 6 | 5-fluoro-6-methylthieno[3,2-b]thiophene-2-carboxylic acid | 0.23 | 3 | 4.2 | 3 |
| 7 | 5-chloro-3-fluorothieno[3,2-b]thiophene-2-carboxylic acid | 0.26 | 3 | 1.1 | 3 |
| 8 | 3-chloro-5,6-difluorothieno[3,2-b]thiophene-2-carboxylic acid | 0.26 | 4 | 1.8 | 4 |
| 9 | 5-fluoro-3-methylthieno[3,2-b]thiophene-2-carboxylic acid | 0.28 | 3 | 1.6 | 3 |
| 10 | 6-chloro-5-fluorothieno[3,2-b]thiophene-2-carboxylic acid | 0.33 | 3 | 3.4 | 3 |
| 11 | 5-chloro-3-(difluoromethyl)thieno[3,2-b]thiophene-2-carboxylic acid | 0.37 | 3 | 2.2 | 3 |
| 12 | 5-chloro-6-fluorothieno[3,2-b]thiophene-2-carboxylic acid | 0.40 | 4 | 1.2 | 2 |
| 13 | 5-chloro-3,6-difluorothieno[3,2-b]thiophene-2-carboxylic acid | 0.47 | 3 | 1.9 | 2 |
| 14 | 5-chloro-3-methylthieno[3,2-b]thiophene-2-carboxylic acid | 0.80 | 3 | Not Tested | |
| 15 | ammonium 3-bromo-5-chlorothieno[3,2-b]thiophene-2-carboxylate | 0.84 | 3 | 2.8 | 3 |
| 16 | 5-chloro-3-ethylthieno[3,2-b]thiophene-2-carboxylic acid | 0.88 | 3 | 3.6 | 3 |
| BT2 | 3,6-dichloro-1-benzothiophene-2-carboxylic acid | 1.3 | 115 | 4.5 | 19 |
| BT2F | 3-chloro-6-fluoro-1-benzothiophene-2-carboxylic acid | 0.81 | 3 | Not Tested | |

Diabetic Animal Model

Mice fed 60% high fat diet (Research Diets 12492) were dosed PO with Example 1 for one day, fasted overnight, and blood glucose was measured with an alpha track glucometer. The animals were dosed again PO with Example 1 the next morning, and one hour later, blood glucose was measured again immediately using an alpha track glucometer (Zoetis, Parsippany, N.J.) to assess fasting glucose levels prior to oral gavage of 1 g/kg dextrose. Blood glucose was measured 15, 30, 60, and 120 minutes after the gavage, and the data were plotted and analyzed as area under the curve using GraphPad Prism 8.0 (GraphPad Software, La Jolla, Calif.). Blood was concomitantly collected in EDTA tubes at the 0, 15 and 30 minute time points, spun down at 10K RPM for 10 minutes. For animals that were dosed with vehicle or Example 1 as above, mean±SEM fasting plasma glucose levels were 237±5 (vehicle, n=18), 230±8 (20 mg/kg, n=18), 221±4 (60 mg/kg, n=40), 206±5 mg/dL (180 mg/kg, n=19). Area under the curve for the glucose tolerance test as percent of vehicle treated group was 100.0±3 (vehicle, n=29), 100±4 (20 mg/kg, n=18), 87±2 (60 mg/kg, n=30), 78±2 (180 mg/kg, n=16).

Heart Failure Rat Model

Dahl salt sensitive male rats (Charles River strain SS/JrHsdMcwiCrl) were fed control diet or 6% high salt diet (iD03121701-AIN-76a rodent diet with added 6% NaCl) for 21 weeks in total. At week 5, the high salt diet-fed rats were dosed PO with 100 mg/kg BT2 or vehicle once daily for the last 16 weeks of study. Echocardiography was performed at week 18 (myocardial performance index (MPI): control diet 0.567±0.034, high salt+vehicle 0.810±0.039, high salt+BT2 0.660±0.030; Isovolumic relaxation time (IVRT): control diet 23.154±0.60 ms, high salt+vehicle 36.507±2.20 ms, high salt+BT2 31.605±1.78 ms; Intraventricular septal thickness at diastole (IVDd): control 2.03±0.088 mm, high salt+vehicle 2.877±0.110 mm, high salt+BT2 2.489±0.089 mm). NT-pro-BNP (MSD K153JKD; control 294.9±26.04 μg/mL, high salt+vehicle 1003.0±200.8 μg/mL, high salt+BT2 503.4±84.96 μg/mL), and proANP (MSD K153MBD; control 33.50±5.4 ng/mL, high salt 65.19±8.3 ng/mL, high salt+BT2 38.81±7.0 ng/mL) levels were measured in plasma using MSD assays at the terminal time point. Heart weights were measured at euthanasia and normalized to tibia length (heart/tibia control 0.033±0.001 g/mm; high salt+vehicle 0.042±0.001 g/mm, high salt+BT2 0.038±0.001 g/mm).

Heart Failure Mouse Model

Male adult mice (8-16-week-old, Charles River strain C57BL6/NCrl) were used for transverse aortic constriction.

One week prior to surgery, animals were dosed with BT2 (40 mg/kg) or vehicle. On the day of surgery, animals were anesthetized, the chest cavity was opened, the aortic area was cleaned, and a silk suture was placed around the transverse aorta. Sham mice were not tied, and TAC mice had the suture tied around a needle. Mice were allowed to recover and were dosed either orally with BT2 (40 mg/kg) once daily or vehicle. Echocardiography was performed serially. Heart weights and lung weights were measured at euthanasia. Data obtained with BT2 have been reported in Sun et al, Circulation. 2016 May 24; 133(21):2038-49. doi: 10.1161/CIRCULATIONAHA.115.020226.

Powder X-ray Diffraction

Powder X-ray diffraction analysis for the compound of Example 1 was conducted using a Bruker AXS D4 Endeavor diffractometer equipped with a Cu radiation source. The divergence slit was set at 0.6 mm while the secondary optics used variable slits. Diffracted radiation was detected by a PSD-Lynx Eye detector. The X-ray tube voltage and amperage were set to 40 kV and 40 mA respectively. Data was collected in the Theta-2Theta goniometer at the Cu wavelength from 3.0 to 40.0 degrees 2-Theta using a step size of 0.020 degrees and a step time of 0.3 second. Samples were prepared by placing them in a silicon low background sample holder and rotated during collection.

For the powder X-ray diffraction analysis of the compound of Example 2, a Bruker AXS D8 Endeavor diffractometer equipped with a Cu radiation source was used. The divergence slit was set at 3 mm continuous illumination. Diffracted radiation was detected by a LYNXEYE EX detector with motorized slits. Both primary and secondary equipped with 2.5 soller slits. The X-ray tube voltage and amperage were set at 40 kV and 40 mA respectively. Data was collected in the Theta-Theta goniometer in a locked couple scan at Cu K-alpha (average) wavelength from 3.0 to 40.0 degrees 2-Theta with an increment of 0.02 degrees, using a scan speed of 0.5 seconds per step. Samples were prepared by placement in a silicon low background sample holder.

Figure 2:
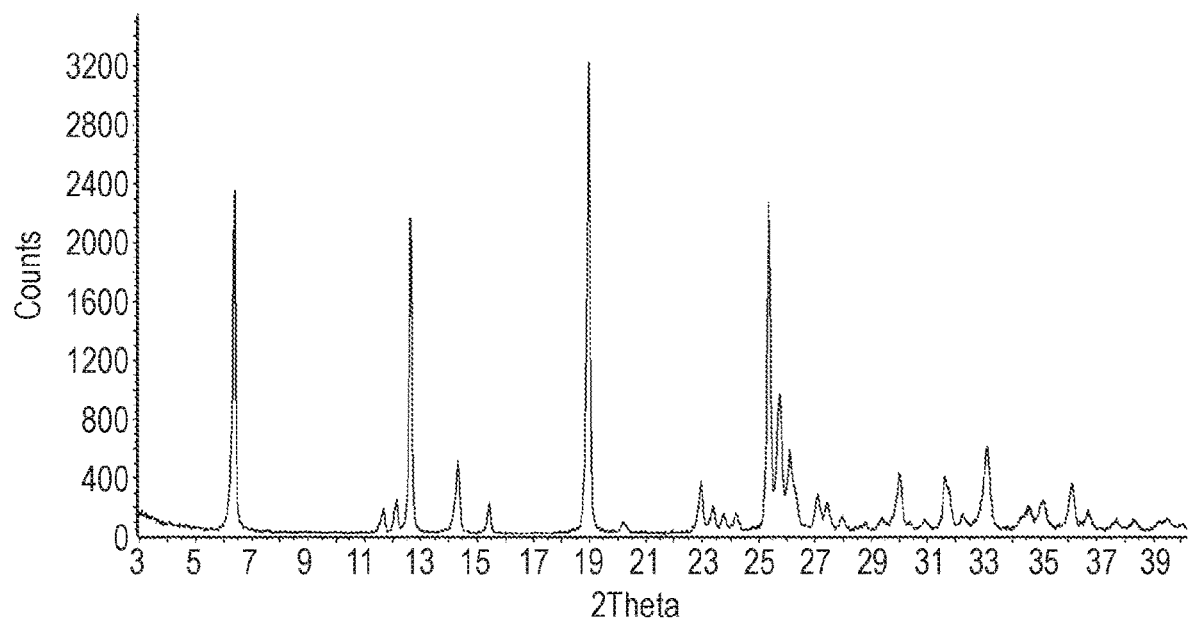
FIG. 2 is a characteristic X-ray powder diffraction pattern showing Example 2, Form 1 (Vertical Axis: Intensity (CPS); Horizontal Axis: Two theta (degrees)).

Data were collected from both instruments for Examples 1 and 2 using Bruker DIFFRAC Plus software and analysis was performed by EVA diffract plus software. The PXRD data file was not processed prior to peak searching. Using the peak search algorithm in the EVA software, peaks selected with a threshold value of 1 were used to make preliminary peak assignments. To ensure validity, adjustments were manually made, the output of automated assignments was visually checked and peak positions were adjusted to the peak maximum. Peaks with relative intensity of ≥3% were generally chosen. The peaks which were not resolved or were consistent with noise were not selected. A typical error associated with the peak position from PXRD stated in USP up to +/−0.2° 2-Theta (USP-941). FIGS. 1 and 2 show the characteristic x-ray powder diffraction patterns of crystalline form 1 of Example 1 and crystalline form 1 of Example 2, respectively. The PXRD data from these figures are further described below.

TABLE 3a

Key PXRD peaks to characterize crystalline material of Example 1, Form 1 and Example 2, Form 1

| Example 1, Form 1 | Example 2, Form 1 |
|---|---|
| Angle 2Θ (°) | Angle 2Θ (°) |
| 11.8, 14.4, 15.5, 18.8 | 6.4, 14.3, 15.4, 19.0 |

TABLE 3b

PXRD peaks for crystalline material of Example 1, Form 1

| Angle 2Θ (°) | Relative intensity (%) | Angle 2Θ (°) | Relative intensity (%) |
|---|---|---|---|
| 11.8 | 17.0 | 26.6 | 6.8 |
| 12.5 | 48.7 | 27.4 | 4.1 |
| 14.4 | 3.5 | 29.9 | 5.3 |
| 15.5 | 100.0 | 31.3 | 5.6 |
| 18.8 | 38.2 | 31.7 | 6.4 |
| 23.3 | 10.5 | 33.2 | 20.3 |
| 24.1 | 3.6 | 35.2 | 15.8 |
| 24.6 | 3.6 | 35.7 | 4.9 |
| 25.2 | 87.0 | 36.0 | 7.0 |
| 25.8 | 26.6 | 37.3 | 8.7 |
| 26.4 | 8.3 | 38.2 | 5.1 |

TABLE 3c

PXRD peaks for crystalline material of Example 2, Form 1

| Angle 2Θ (°) | Relative intensity (%) | Angle 2Θ (°) | Relative intensity (%) |
|---|---|---|---|
| 6.4 | 72.4 | 25.8 | 28.6 |
| 7.6 | 4.4 | 26.1 | 16.7 |
| 7.3 | 6.8 | 27.1 | 6.6 |
| 12.7 | 67.2 | 27.4 | 5.3 |
| 14.3 | 13.9 | 30.0 | 10.6 |
| 15.4 | 6.5 | 31.6 | 10.6 |
| 19.0 | 100.0 | 33.1 | 17.4 |
| 23.0 | 10.7 | 34.6 | 4.5 |
| 23.4 | 4.9 | 35.1 | 5.8 |
| 24.2 | 3.4 | 36.1 | 9.5 |
| 25.4 | 69.3 | 36.7 | 3.8 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of Formula I

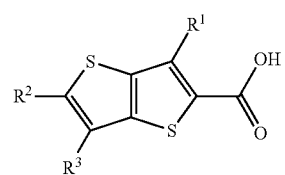

wherein $R^1$ is H, bromo, chloro, fluoro, $(C_1-C_2)$alkyl, or $(C_1-C_2)$fluoroalkyl;

$R^2$ is fluoro or chloro, wherein if $R^1$ is chloro and $R^3$ is H then $R^2$ is fluoro; and R³ is H, chloro, fluoro, methyl, or (C₁)fluoroalkyl, wherein if R¹ is H then R³ is chloro, fluoro, methyl or (C₁)fluoroalkyl;
or a pharmaceutically acceptable salt of said compound.

2. A compound of claim 1 wherein
R¹ is H, bromo, chloro, or difluoro(C₁)alkyl;
R² is fluoro; and
R³ is H or fluoro wherein if R¹ is H then R³ is fluoro;
or a pharmaceutically acceptable salt of said compound.

3. A compound of claim 1 selected from the group consisting of:
3-chloro-5-fluorothieno[3,2-b]thiophene-2-carboxylic acid;
3-bromo-5-fluorothieno[3,2-b]thiophene-2-carboxylic acid;
3-(difluoromethyl)-5-fluorothieno[3,2-b]thiophene-2-carboxylic acid;
5,6-difluorothieno[3,2-b]thiophene-2-carboxylic acid; and
3,5-difluorothieno[3,2-b]thiophene-2-carboxylic acid;
or a pharmaceutically acceptable salt thereof.

4. A compound wherein the compound is

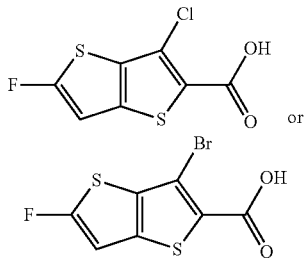

or a pharmaceutically acceptable salt of said compound.

5. A compound wherein the compound is 3-chloro-5-fluorothieno[3,2-b]thiophene-2-carboxylic acid or a pharmaceutically acceptable salt thereof.

6. A compound according to claim 5 wherein the compound is 3-chloro-5-fluorothieno[3,2-b]thiophene-2-carboxylic acid.

7. A method of treating fatty liver, nonalcoholic fatty liver disease, nonalcoholic steatohepatitis, nonalcoholic steatohepatitis with liver fibrosis, nonalcoholic steatohepotitis with cirrhosis or nonalcoholic steatohepatitis with cirrhosis and hepatocellular carcinoma comprising administering to a human in need of such treatment a therapeutically effective amount of a compound of claim 5 or a pharmaceutically acceptable salt thereof.

8. The method as recited in claim 7 wherein nonalcoholic steatohepatitis is treated.

9. A method of treating heart failure, congestive heart failure, coronary heart disease, peripheral vascular disease, renovascular disease, pulmonary hypertension, vasculitis, acute coronary syndromes and modification of cardiovascular risk comprising administering to a human in need of such treatment a therapeutically effective amount of a compound of claim 5 or a pharmaceutically acceptable salt thereof.

10. The method as recited in claim 9 wherein heart failure is treated.

11. A method of treating Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, diabetic retinopathy, macular degeneration, cataract, diabetic nephropathy, glomerulosclerosis, chronic renal failure, diabetic neuropathy, metabolic syndrome, syndrome X, hyperglycemia, hyperinsulinemia, hypertriglyceridemia, insulin resistance, impaired glucose metabolism, skin and connective tissue disorders, foot ulcerations and ulcerative colitis, endothelial dysfunction and impaired vascular compliance, hyper apo B lipoproteinemia, and maple syrup urine disease comprising administering to a human in need of such treatment a therapeutically effective amount of a compound of claim 5 or a pharmaceutically acceptable salt thereof.

12. The method as recited in claim 11 wherein Type II diabetes mellitus is treated.

13. A method of treating hepatocellular carcinoma, kidney renal clear cell carcinoma, head and neck squamous cell carcinoma, colorectal adenocarcinoma, mesothelioma, stomach adenocarcinoma, adrenocortical carcinoma, kidney papillary cell carcinoma, cervical and endocervical carcinoma, bladder urothelial carcinoma, lung adenocarcinoma comprising administering to a human in need of such treatment a therapeutically effective amount of a compound of claim 5 or a pharmaceutically acceptable salt thereof.

14. The method as recited in claim 13 wherein hepatocellular carcinoma or colorectal adenocarcinoma is treated.

15. A pharmaceutical composition which comprises a therapeutically effective amount of a compound of claim 5 or a pharmaceutically acceptable salt thereof and a pharmaceutically acceptable carrier, vehicle or diluent.

16. A pharmaceutical combination composition comprising: a therapeutically effective amount of a composition comprising:
a first compound, said first compound being a compound of claim 5, or a pharmaceutically acceptable salt thereof;
a second compound, said second compound being an anti-diabetic agent; a non-alcoholic steatohepatitis treatment agent, a non-alcoholic fatty liver disease treatment agent or an anti-heart failure treatment agent and
a pharmaceutical carrier, vehicle or diluents.

17. The pharmaceutical combination composition as recited in claim 16 wherein said second compound is 4-(4-(1-isopropyl-7-oxo-1,4,6,7-tetrahydrospiro[indazole-5, 4'-piperidine]-t-carbonyl)-6-methoxypyridin-2-yl)benzoic acid; [(1R,5S,6R)-3-{2-[(2S)-2-methylazetidin-1-yl]-6-(trifluoromethyl)pyrimidin-4-yl}-3-azabicyclo[3.1.0]hex-6-yl] acetic acid; 2-[(1R,3R,5S)-3-({5-cyclopropyl-3-[2 -(trifluoromethoxy)phenyl]-1,2-oxazol-4-yl}methoxy)-8-azabicyclo [3.2.1]octan-8-yl]-4-fluoro-1,3-benzothiazole-6-carboxylic acid; (S)-2-(5-((3-ethoxypyridin-2-yl)oxy)pyridin-3-yl)-N-(tetrahydrofuran-3-yl)pyrimidine-5-carboxamide; or 2-[(4-{6-[(4-cyano-2-fluorobenzyl)oxy]pyridin-2-yl}piperidin-1-yl)methyl]-1-[(2S)-oxetan-2-ylmethyl]-1H-benzimidazole-6-carboxylic acid, or a pharmaceutically acceptable salt thereof.

18. The pharmaceutical combination composition as recited in claim 16 wherein said non-alcoholic steatohepatitis treatment agent or non-alcoholic fatty liver disease treatment agent is an ACC inhibitor, a KHK inhibitor, a DGAT-2 inhibitor, an FXR agonist, metformin, incretin analogs, or an incretin receptor modulator.

19. The pharmaceutical combination composition as recited in claim 16 wherein said anti-diabetic agent is an SGLT-2 inhibitor, metformin, incretin analogs, an incretin receptor modulator, a DPP-4 inhibitor, or a PPAR agonist.

20. The pharmaceutical combination composition as recited in claim 19 wherein said anti-diabetic agent is metfomin, sitagliptin or ertuglifozin.

21. The pharmaceutical combination composition as recited in claim 16 wherein said anti-heart failure agent is an ACE inhibitor, an SGLT2 inhibitor, an angiotensin receptor blocker, a neprilysin inhibitor, an angiotensin-receptor blocker/neprilysin inhibitor, a beta adrenergic receptor blocker, a calcium channel blocker, or a vasodilator.

22. A crystal comprising a compound of claim 5 having the structure:

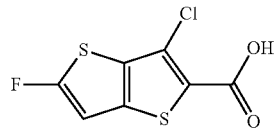

or a pharmaceutically acceptable salt thereof.

23. The crystal of claim 22 having a powder x-ray diffraction pattern comprising 2-theta values of (CuKα radiation, wavelength of 1.54056 Å) 11.8±0.2, 14.4±0.2, 15.5±0.2, and 18.8±0.2.

* * * * *